(12) United States Patent
Occhialini et al.

(10) Patent No.: US 7,473,299 B2
(45) Date of Patent: Jan. 6, 2009

(54) WEIGHT-OPTIMIZED PORTABLE OXYGEN CONCENTRATOR

(75) Inventors: James Michael Occhialini, New Tripoli, PA (US); Roger Dean Whitley, Allentown, PA (US); Glenn Paul Wagner, Fogelsville, PA (US); Matthew James LaBuda, Fogelsville, PA (US); Craig E. Steigerwalt, Slatington, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/845,190

(22) Filed: Aug. 27, 2007

(65) Prior Publication Data

US 2007/0289446 A1 Dec. 20, 2007

Related U.S. Application Data

(62) Division of application No. 10/851,858, filed on May 21, 2004, now Pat. No. 7,279,029.

(51) Int. Cl.
*B01D 53/02* (2006.01)
(52) U.S. Cl. ............................... 95/96; 96/121; 96/130; 128/205.12
(58) Field of Classification Search ............ 95/96; 96/121, 130; 128/205.12
See application file for complete search history.

(56) References Cited

U.S. PATENT DOCUMENTS

| | | |
|---|---|---|
| 6,471,744 B1 | 10/2002 | Hill |
| 6,478,850 B1 | 11/2002 | Warren |
| 6,520,176 B1 | 2/2003 | Dubois et al. |
| 6,547,851 B2 | 4/2003 | Warren |

(Continued)

FOREIGN PATENT DOCUMENTS

WO   WO 03/092817 A1   11/2003

OTHER PUBLICATIONS

Paul M. Mathias, et al., "Correlation of Multicomponent Gas Adsorption by the Dual-Site Langmuir Model. Application to Nitrogen/Oxygen Adsorption on 5A-Zeolite", Industrial & Engineering Chemistry Research, vol. 35, No. 7, pp. 2477-2483, 1996.

(Continued)

*Primary Examiner*—Robert A Hopkins
(74) *Attorney, Agent, or Firm*—John M. Fernbacher

(57) ABSTRACT

System for producing an oxygen-rich gas comprising (a) a primary gas mover including a first and a second compressor, wherein the primary gas mover is characterized by a weight $W_p$; (b) a drive motor adapted to drive the first and second compressors; (c) a rechargeable power supply characterized by a weight, $W_b$; and (d) a pressure/vacuum swing adsorption unit adapted to separate the pressurized feed air into an oxygen-rich product at a product flow rate $F_p$ and an oxygen-depleted waste gas, wherein the adsorption unit comprises a plurality of adsorber beds containing an adsorbent and characterized by a total adsorbent weight $W_a$; and wherein the combined weight, $W_t$, of the adsorbent, the primary gas mover, and the rechargeable power supply is characterized by the expression $$0.75\, F_p < W_t < 2.02\, F_p$$

where $F_p$ is in liters per min (at 23° C. and 1 atma pressure), and $W_a$, $W_p$, and $W_b$ are in pounds.

7 Claims, 13 Drawing Sheets

U.S. PATENT DOCUMENTS

| | | |
|---|---|---|
| 6,551,384 B1 | 4/2003 | Ackley et al. |
| 6,558,451 B2 * | 5/2003 | McCombs et al. ............ 95/98 |
| 6,629,525 B2 | 10/2003 | Hill et al. |
| 6,764,534 B2 | 7/2004 | McCombs et al. |
| 6,889,710 B2 | 5/2005 | Wagner |
| 7,273,051 B2 | 9/2007 | Whitley et al. |
| 2001/0001939 A1 | 5/2001 | Smolarek et al. |
| 2002/0096174 A1 | 7/2002 | Hill et al. |
| 2003/0005928 A1 | 1/2003 | Appel et al. |
| 2005/0160905 A1 | 7/2005 | Whitley et al. |

OTHER PUBLICATIONS

A.L. Myers; "Activity Coefficients of Mixtures Adsorbed on Heterogeneous Surfaces"; Department of Chemical Engineering; University of Pennsylvania; AlChE Journal; vol. 29, No. 4; Jul. 1983; pp. 691-693.

* cited by examiner

WEIGHT-OPTIMIZED PORTABLE OXYGEN CONCENTRATOR

CROSS-REFERENCE TO RELATED APPLICATIONS

This is a divisional of application Ser. No. 10/851,858, filed May 21, 2004 now U.S. Pat. No. 7,279,029, which is incorporated herein by reference in its entirety.

BACKGROUND OF THE INVENTION

The supply of therapeutic oxygen to patients in homes and other residential settings is an important and growing market in the health care industry. A segment of this market includes the development and commercialization of portable oxygen concentrators, particularly units that can be carried easily by patients requiring continuous oxygen therapy. A portable and easily-carried oxygen supply may be provided by stored liquid or compressed oxygen with an appropriate vaporization or pressure regulation system and a gas delivery cannula. Alternatively and preferably, oxygen may be supplied by a small air separation device carried by the patient that supplies gaseous oxygen at the desired purity, flow rate, and pressure. Power for operating the device can be provided by a rechargeable power supply, typically a rechargeable battery. The small air separation device may be an adsorption-based system using a pressure swing adsorption (PSA) process.

Respiratory oxygen usage rates typically range up to about 5 lpm (liters per minute at 23° C. and 1 atma pressure) for ambulatory patients with moderate oxygen requirements. The design of an easily-carried, rechargeable, portable oxygen concentrator in this product range should achieve an appropriate balance among product gas flow rate, weight, and power supply life or run time (i.e., the operating time between power supply recharges). This balance requires the proper choice of numerous operating and design parameters and presents a significant challenge to engineering designers. In a small adsorptive air separation unit, for example, design parameters may include product purity, product delivery pressure, type of process cycle, process cycle pressure envelope, adsorbent, number and dimensions of adsorbent beds, type of gas mover, type of power supply, gas flow control methods, electrical control systems, and materials of construction.

There is a need in the art for methods to design portable adsorption-based oxygen generation systems that provide the required gas supply rates and run times with minimum system weight. This need can be met by optimization methods that enable designers to balance these requirements while specifying appropriate process and mechanical parameters for these systems.

BRIEF SUMMARY OF THE INVENTION

This need for optimized design of small, easily-carried, adsorption-based oxygen concentrators is met by the various embodiments of the present invention. As described in detail herein, it has been found that a minimum weight range can be determined for an adsorption-based system for any operable combination of product flow rate, product purity, product delivery pressure, and run time. This may be achieved by determining the weight of each variable-weight system component as a function of a selected process parameter, adding the weights of these components at various values of the selected parameter, and generating a curve of variable weight vs. the selected parameter. This curve generally exhibits a minimum weight in a preferred range of the selected process parameter. The selected process parameter is the minimum bed pressure during the process cycle.

An embodiment of the invention relates to a system for producing an oxygen-rich gas comprising (a) a primary gas mover including a first compressor adapted to compress atmospheric air to provide pressurized feed air and a second compressor adapted to compress a waste gas from subatmospheric pressure to atmospheric pressure, wherein the primary gas mover is characterized by a weight $W_p$;

(b) a drive motor adapted to drive the first and second compressors;

(c) a rechargeable power supply adapted to supply power to the drive motor, wherein the rechargeable power supply is characterized by a weight $W_b$; and (d) a pressure/vacuum swing adsorption unit adapted to separate the pressurized feed air into an oxygen-rich product at a product flow rate $F_p$ and an oxygen-depleted waste gas, wherein the adsorption unit comprises a plurality of adsorber beds containing an adsorbent, wherein the total amount of the adsorbent contained in the adsorber beds is characterized by a total adsorbent weight $W_a$;

wherein the combined weight, $W_t$, of the adsorbent, the primary gas mover, and the rechargeable power supply may be characterized by the expression $$0.75 F_p < W_t < 2.02 F_p$$

where $F_p$ is in liters per min (at 23° C. and 1 atma pressure) and $W_a$, $W_p$, and $W_b$ are in pounds.

The battery may be characterized by an operating run time in hours, $t_r$, between maximum and minimum working charge, and the system may be further characterized by any of the expressions $$0.21 F_p < W_a < 0.61 F_p,$$

$$0.36 F_p < W_p < 0.70 F_p,$$

$$0.18 F_p < W_b < 0.71 F_p, \text{ and}$$

$$0.10 F_p t_r < W_b < 0.40 F_p t_r.$$

The plurality of adsorber beds may comprise four or more beds, and may consist of four beds.

Each of the first and second compressors may be selected from the group consisting of scroll, diaphragm, piston, and rotary vane compressors. The first and second compressors may be scroll-type compressors. The system may further comprise a conserver.

The system may have a total weight of less than 12 pounds, may have a total weight of less than 10 pounds, and may have a total weight of less than 8 pounds.

The adsorbent may be selected from the group consisting of zeolite X exchanged with one or more metallic cations selected from the group consisting of lithium, calcium, zinc, copper, sodium, potassium, and silver. The adsorber beds may further comprise an additional adsorbent selective for the adsorption of water and carbon dioxide from air and wherein the additional adsorbent is selected from the group consisting of (1) activated alumina and (2) zeolite X exchanged with one or more metallic cations selected from the group consisting of lithium, sodium, and potassium.

The rechargeable power supply may be a battery. Alternatively, the rechargeable power supply may be a fuel cell.

The system may further comprise an external case surrounding the primary gas mover, drive motor, rechargeable power supply, and pressure/vacuum swing adsorption system, and a user display/control panel mounted on the outer side of the case. This system may have a total weight of less than 12 pounds, may have a total weight of less than 10 pounds, and may have a total weight of less than 8 pounds.

The system for producing an oxygen-rich gas may comprise (a) a primary gas mover including a first compressor adapted to compress atmospheric air to provide pressurized feed air and a second compressor adapted to compress a waste gas from subatmospheric pressure to atmospheric pressure, wherein the primary gas mover is characterized by a weight $W_p$;

(b) a drive motor adapted to drive the first and second compressors;

(c) a rechargeable power supply adapted to supply power to the drive motor, wherein the rechargeable power supply is characterized by a weight, $W_b$, and an operating run time, $t_r$, between maximum and minimum working charge; and (d) a pressure/vacuum swing adsorption unit adapted to separate the pressurized feed air into an oxygen-rich product at a product flow rate $F_p$ and an oxygen-depleted waste gas, wherein the adsorption unit comprises a plurality of adsorber beds containing adsorbent, wherein the total amount of the adsorbent contained in the adsorber beds is characterized by a total adsorbent weight $W_a$;

wherein the system may be characterized by any of the expressions $$0.21\, F_p < W_a < 0.61\, F_p,$$

$$0.36\, F_p < W_p < 0.70\, F_p,$$

$$0.18\, F_p < W_b < 0.71\, F_p, \text{ and}$$

$$0.10\, F_p t_r < W_b < 0.40\, F_p t_r,$$

where $F_p$ is in liters per min (at 23° C. and 1 atma pressure), $t_r$ is in hours, and $W_a$, $W_p$ and $W_b$, are in pounds.

The system may further comprise additional elements including electrical wiring and control systems, a case or housing, and a user display/control panel mounted on the outer side of the housing, wherein the oxygen generation system and the additional elements are combined to form a portable oxygen concentrator, and means for the user to carry the portable concentrator unit.

Another embodiment of the invention pertains to a method for producing an oxygen-rich product gas comprising (a) providing a primary gas mover including a first compressor for compressing atmospheric air to provide pressurized feed air and a second compressor adapted to compress an oxygen-depleted waste gas from subatmospheric pressure to atmospheric pressure, a drive motor for driving the first and second compressors, and a rechargeable battery for providing power to the drive motor, wherein the rechargeable power supply is characterized by an operating run time between maximum and minimum working charge;

(b) providing a pressure/vacuum swing adsorption system adapted to separate the pressurized feed air into the oxygen-rich product gas and the oxygen-depleted waste gas, wherein the adsorption system comprises a plurality of adsorber beds containing adsorbent; and (c) operating each of the adsorber beds in turn through an adsorption cycle including at least the repeating steps of feed/provide product, depressurization, evacuation, and repressurization;

wherein the method may be characterized by any of the operating parameters (1) the rechargeable battery provides between 0.02 and 0.17 KWh of power during the operating run time between maximum and minimum working charge;

(2) the total working capacity of the adsorbent in each adsorber bed during the adsorption cycle is between $1.2 \times 10^{-4}$ and $6.7 \times 10^{-4}$ lbmoles of nitrogen;

(3) the first compressor moves between $1.14 \times 10^{-4}$ and $4.01 \times 10^{-4}$ lbmoles of pressurized feed air during the feed/provide product step; and (4) the second compressor moves between $3.47 \times 10^{-4}$ and $9.96 \times 10^{-4}$ lbmoles of waste gas during the depressurization and evacuation steps.

The pressure/vacuum swing adsorption system may have four adsorber beds and each of the adsorber beds may undergo in turn a series of adsorption cycle steps which comprise (A) a feed/make product step wherein the pressurized feed air is introduced into a feed end of the bed while the oxygen-enriched product gas is withdrawn from a product end of the bed;

(B) a feed/make product/provide repressurization step wherein the pressurized feed air is introduced into a feed end of the bed while an oxygen-enriched product gas is withdrawn from a product end of the bed, and wherein a portion of the product gas is used for pressurizing another bed undergoing its final repressurization step;

(C) a depressurization step in which the bed is depressurized by withdrawing gas therefrom, wherein at least a portion of the gas withdrawn therefrom is transferred to another bed undergoing a repressurization step;

(D) a provide purge step in which the bed is further depressurized by withdrawing gas therefrom, wherein at least a portion of the gas withdrawn therefrom is transferred to another bed undergoing a purge step;

(E) an evacuation step in which gas is withdrawn from the feed end of the bed until the bed reaches a minimum subatmospheric bed pressure;

(F) a purge step in which the bed is purged by introducing purge gas into the product end of the bed while continuing to evacuate the bed, wherein the purge gas is provided from another bed undergoing step (D);

(G) a repressurization step in which pressurization gas is introduced into the product end of the bed, wherein the pressurization gas is provided from another bed undergoing step (C); and (H) a final repressurization step in which product gas from another bed is introduced into the product end of the bed.

The minimum bed pressure may be between 0.25 and 1.0 atma, and may be between 0.45 and 0.8 atma. The pressure of the oxygen-enriched product gas may be between 1.2 and 1.6 atma. The oxygen-enriched product gas may be provided at a flow rate in the range of 0.5 to 3.0 liters per min (defined at 23° C. and 1 atma pressure).

An alternative embodiment of the invention is directed to a method for producing an oxygen-rich product gas comprising (a) providing a primary gas mover including a first compressor for compressing atmospheric air to provide pressurized feed air and a second compressor adapted to compress an oxygen-depleted waste gas from subatmospheric pressure to atmospheric pressure, a drive motor for driving the first and second compressors, and a rechargeable battery for providing power to the drive motor, wherein the rechargeable power supply is characterized by an operating run time between maximum and minimum working charge;

(b) providing a pressure/vacuum swing adsorption unit adapted to separate the pressurized feed air into the oxygen-rich product gas and the oxygen-depleted waste gas, wherein the adsorption unit comprises a plurality of adsorber beds containing adsorbent selective for the adsorption of nitrogen from air; and (c) operating each of the adsorber beds in turn through an adsorption cycle including at least the repeating steps of feed/provide product, depressurization, evacuation, and repressurization;

wherein the minimum pressure in the evacuation step may be between 0.35 and 1.00 atma.

Another embodiment of the invention relates to a method for the design of a portable pressure/vacuum swing adsorption oxygen concentrator system comprising (a) defining design parameters including at least a product flow rate, a product purity, a product delivery pressure, a pressure/vacuum swing adsorption process cycle, the number of adsorber vessels, an adsorbent contained in the adsorber vessels, the type of gas mover, the type of regenerable power supply to provide power to the drive motor, and the run time of the regenerable power supply between maximum and minimum working charge;

(b) selecting a series of minimum bed pressures pressures below atmospheric pressure and determining for each of the minimum bed pressures the required weights of the gas mover, the power supply, and the adsorbent contained in the adsorber vessels, wherein each minimum bed pressure is a lowest bed pressure in the pressure/vacuum swing adsorption process cycle;

(c) adding the weights of the adsorbent, the gas mover, and the power supply determined in (b) for each value of the minimum bed pressure to provide a total weight of the adsorbent, the gas mover, and the power supply as a function of the minimum bed pressure; and (d) selecting a range of the minimum bed pressures that corresponds to a range of minimum combined weight of the adsorbent, the gas mover, and the power supply.

The range of minimum bed pressures may be between 0.45 and 0.8 atma.

DETAILED DESCRIPTION OF THE INVENTION

The embodiments of the invention described herein are directed to methods for designing and optimizing the weight of small pressure/vacuum swing adsorption (PVSA) systems utilized, for example, in portable and user-carried medical oxygen concentrator systems. It was found in the development of the embodiments of the present invention that a minimum weight or desirable range of weights can be determined for the PVSA system for any operable combination of product flow rate, product purity, product delivery pressure, and run time. This may be achieved by determining the weight of each variable-weight system component as a function of a selected process parameter, adding the weights of these components at various values of the selected parameter, and generating a curve of variable weight vs. the selected parameter. This curve generally exhibits a desirable minimum weight or range of minimum weights as a function of the selected process parameter. This selected process parameter may be the minimum bed pressure during regeneration in the PVSA cycle.

In the PVSA process described herein, the adsorber bed pressures vary between superatmospheric pressure and subatmospheric pressure during each cycle as described below. This differs from a pressure swing adsorption (PSA) process in which the operating pressure range includes bed pressures above atmospheric pressure and may include bed pressures approaching atmospheric pressure at the end of the depressurization step. Subatmospheric pressures are not utilized in a PSA process.

Figure 1:
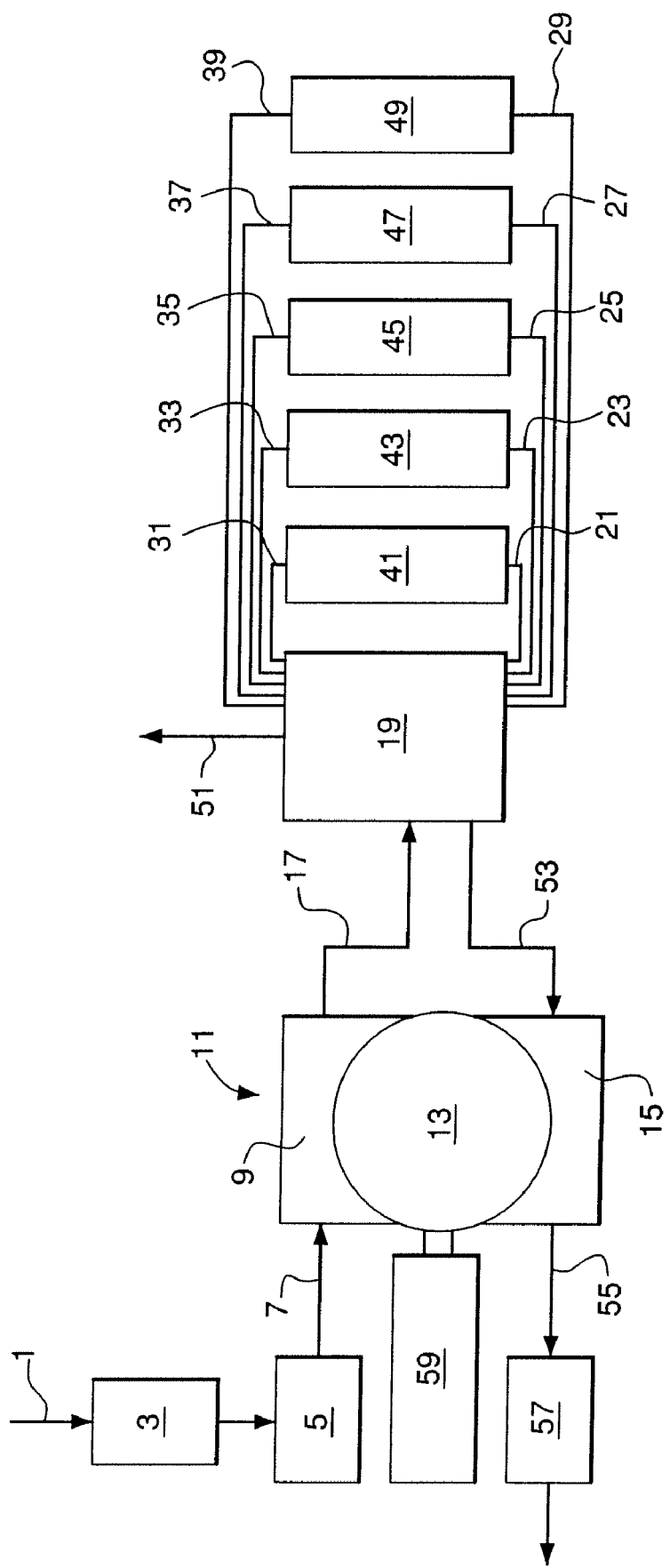
FIG. 1 is a schematic flow diagram of an exemplary pressure/vacuum swing adsorption system for embodiments of the present invention.

An exemplary PVSA process and system that may be designed according to embodiments of the invention is shown for the purpose of illustration in FIG. 1. Atmospheric air 1 is drawn through filter 3, inlet silencer 5, and line 7 by first or feed air compressor 9. Feed air compressor 9 is a part of primary gas mover 11 which also includes drive motor 13 and second or vacuum waste gas compressor 15. Pressurized feed air at 1.15 to 1.80 atma is discharged from the compressor and flows through air feed line 17 to rotary valve assembly 19, which is in flow communication with adsorber bed feed lines 21, 23, 25, 27, and 29, adsorber bed product lines 31, 33, 35, 37, and 39, air feed line 17, product line 51, and waste gas line 53. In this exemplary PVSA system, five adsorber beds 41, 43, 45, 47, and 49 are used, although any number of multiple beds may be used. An optional product gas storage tank (not shown) may be used if desired. A cannula (not shown) may be connected to product line 51 to deliver product gas to the user.

Each adsorber bed contains adsorbent selective for the adsorption of water, carbon dioxide, and nitrogen from air. This adsorbent may be selected from the group consisting of zeolite X exchanged with one or more metallic cations selected from the group consisting of lithium, calcium, zinc, copper, sodium, potassium, and silver. The zeolite X may have a ratio of silicon to aluminum of about 1 to about 1.25. The adsorbent may be formed into beads, extrudates, or other shapes known in the art, using binder materials or without binder materials (also known as binderless). The adsorbent typically adsorbs water and carbon dioxide more strongly than nitrogen, and therefore the initial adsorbent adjacent to the feed air inlet of an adsorber will preferentially remove water and carbon dioxide. Dry, carbon dioxide-free air from this initial adsorbent region then passes to the remainder of the adsorbent in the adsorber, where the nitrogen is selectively adsorbed to provide the oxygen-enriched product gas. The initial adsorbent adjacent to the feed air inlet thereby provides pretreatment by removing water and carbon dioxide prior to nitrogen removal.

Optionally, each adsorber bed also may contain pretreatment adsorbent selective for the adsorption of water and carbon dioxide from air, and this adsorbent may be selected from the group consisting of (1) activated alumina and (2) zeolite X exchanged with one or more metallic cations selected from the group consisting of lithium, sodium, and potassium. Typically, the water-selective adsorbent (if used) would form a layer located adjacent the feed end of the adsorber bed and may comprise 10 to 40% of the total adsorbent in the adsorber bed. In this option, the remainder of the bed would contain the adsorbent described above and would selectively adsorb nitrogen from the water and carbon dioxide-free air from the pretreatment adsorbent layer.

Vacuum waste gas compressor 15 withdraws oxygen-depleted PVSA waste gas through line 53, typically at subatmospheric pressure, and discharges the gas via line 57 and silencer 57 to the atmosphere. Electric power for drive motor 13 is provided by rechargeable power supply 59, which may be a rechargeable battery of any type known in the art. Alternatively, the rechargeable power supply may be a portable fuel cell system comprising a fuel cell and portable fuel storage means. The fuel may be hydrogen or methanol.

Feed air compressor 9 and vacuum waste gas compressor 15 may be any type of compressor known in the art and may be selected from scroll, diaphragm, piston, and rotary vane compressors. The feed air and vacuum waste gas compressors may be driven in tandem by a single drive motor and may be driven by a common drive shaft. Scroll compressors are well-suited for service with the air separation device described herein. Feed air compressor 9 and vacuum waste gas compressor 15 may be combined in a single combined scroll-type primary gas mover.

Rotary valve assembly 19 is designed for a specific PVSA cycle and a specific number of adsorber beds. The assembly includes a first rotary valve connected to lines 21, 23, 25, 27, and 29 that are attached to the feed ends of adsorbent beds 41, 43, 45, 47, and 49, respectively. The first rotary valve also is connected to air feed line 17 and waste gas line 53. This first rotary valve enables appropriate flow communication among any of the feed ends of the adsorbent beds, the air feed line, and the waste gas line according to predetermined process cycle steps as described below. A second rotary valve is connected to lines 31, 33, 35, 37, and 39 that are attached to the product ends of the adsorbent beds, respectively, and also is connected to product line 51. This second rotary valve enables appropriate flow communication among any of the product ends of the adsorbent beds and the product line according to predetermined process cycle steps as described below. The two rotary valves may be operated by a single drive motor and may rotate at the same rotational rate. Rotary valves of this type are described, for example, in a copending U.S. patent application having Ser. No. 10/295,144 filed on Nov. 15, 2002. This patent application is incorporated herein by reference.

The operation of the PVSA system of FIG. 1 may be illustrated by an exemplary PVSA cycle summarized in Table 1.

TABLE 1

Process Cycle Steps for Exemplary PVSA System

| Step Number | Description | Duration, Sec. |
|---|---|---|
| 1 | Feed/make product/provide purge | 1.0 |
| 2 | Feed/make product/provide repress. gas | 1.0 |
| 3 | provide $1^{st}$ repressurization gas | 1.0 |
| 4 | provide $2^{nd}$ repressurization gas | 1.0 |
| 5 | Idle step | 1.0 |
| 6 | Evacuation | 1.0 |
| 7 | Purge with product gas | 1.0 |
| 8 | Receive $2^{nd}$ repressurization gas | 1.0 |
| 9 | Receive $1^{st}$ repressurization gas | 1.0 |
| 10 | Repressurize with product gas | 1.0 |

During the initial portion of Step 1, the feed step, there may be a short period of feed pressurization before product gas flows from the bed. During evacuation in Step 6, a minimum bed pressure is attained, which is defined as the lowest pressure during this step. The duration of this exemplary 10 second cycle, or the duration of any step in the cycle, may be modified as required to meet various process or product requirements.

A cycle chart is given in Table 2 to show the relationship of cycle steps among the five adsorbent beds, wherein each bed in turn passes through steps 1-10 of Table 1.

TABLE 2

PVSA Cycle Chart

| Bed | Step Number | | | | | | | | | |
|---|---|---|---|---|---|---|---|---|---|---|
| 41 | 1 | 2 | 3 | 4 | 5 | 6 | 7 | 8 | 9 | 10 |
| 43 | 9 | 10 | 1 | 2 | 3 | 4 | 5 | 6 | 7 | 8 |
| 45 | 7 | 8 | 9 | 10 | 1 | 2 | 3 | 4 | 5 | 6 |
| 47 | 5 | 6 | 7 | 8 | 9 | 10 | 1 | 2 | 3 | 4 |
| 49 | 3 | 4 | 5 | 6 | 7 | 8 | 9 | 10 | 1 | 2 |

The use of Tables 1 and 2 together with FIG. 1 will enable the skilled person to understand this exemplary PVSA process cycle. Modifications to this particular cycle may be made if desired, and other types of PVSA cycles may be used as appropriate.

As an alternative embodiment to the five bed PVSA system and cycle described above, a four bed system and cycle may be used. This four bed system would be a modification of the system of FIG. 1 wherein adsorber bed 49, adsorber bed feed line 29, and adsorber product line 39 are deleted. Rotary valve 19 would be designed for four beds instead of five beds. In this alternative cycle, only one pressurization gas transfer step is used compared with two such steps in the five bed cycle of Table 1. Table 3 presents the four bed cycle steps and Table 4 presents a cycle chart for the four bed cycle (note that bed 49 of FIG. 1 is deleted for the four bed system).

TABLE 3

Process Cycle Steps for Exemplary 4-Bed PVSA System

| Step Number | Description | Duration, Sec. |
|---|---|---|
| 1 | Feed/make product | 1.0 |
| 2 | Feed/make product/provide repress. gas | 1.0 |
| 3 | Provide repressurization gas | 1.0 |
| 4 | Provide purge | 1.0 |
| 5 | Evacuation | 1.0 |
| 6 | Purge | 1.0 |
| 7 | Receive repressurization gas | 1.0 |
| 8 | Repressurize with product gas | 1.0 |

TABLE 4

4-Bed PVSA Cycle Chart

| Bed | Step Number | | | | | | | |
|---|---|---|---|---|---|---|---|---|
| 41 | 1 | 2 | 3 | 4 | 5 | 6 | 7 | 8 |
| 43 | 7 | 8 | 1 | 2 | 3 | 4 | 5 | 6 |
| 45 | 5 | 6 | 7 | 8 | 1 | 2 | 3 | 4 |
| 47 | 3 | 4 | 5 | 6 | 7 | 8 | 1 | 2 |

A complete portable user-carried oxygen concentrator system typically includes a number of components in addition to those illustrated by the exemplary PVSA system of FIG. 1. These additional components may include, for example, any of the following features: electrical wiring and control systems;; structural elements; a case or housing; a user display/control panel mounted on the outer side of the housing; a conserver; a product tank; and means for the user to carry the concentrator unit such as a handle, carrying strap, or dual shoulder straps. The total weight of the portable user-carried oxygen concentrator system thus is the combined weight of (a) the variable-weight components earlier described (i. e., the adsorbent, primary gas mover, and the battery) and (b) the additional components described immediately above.

Portable user-carried oxygen concentrator systems such as that those described above using four or five beds may be designed to meet desirable criteria such as, for example, a continuous oxygen product flow of up to 3 lpm, an easily-carried weight, and an operating time on a single power supply recharge of at least 1-2 hours. A system meeting these criteria would provide more freedom and a higher standard of living for an ambulatory patient and would be an attractive product offering for a supplier of oxygen concentrators.

Embodiments of the PVSA oxygen concentrator system described above preferably meet these criteria and provide the patient with an oxygen-enriched product of at least 85 mole % oxygen purity. The portable oxygen concentrator system should be easily carried by the patient and have a total weight of less than 12 pounds, preferably less than 10 pounds, and most preferably less than 8 pounds. Because patients needing oxygen therapy usually are ill, minimum system weight is extremely important. As mentioned earlier, designing these systems for minimum weight is a significant engineering challenge.

When the product flow rate, product purity, product delivery pressure, and system run time are specified, the total weight of the oxygen concentrator system consists of some components whose weights depend on the PVSA operating conditions and other components whose weights are essentially independent of PVSA operating conditions. The variable-weight components in this scenario include the power supply (e.g., battery), the weight of adsorbent in the adsorbent beds, and the weight of the primary gas mover, i.e., the feed air compressor and vacuum waste gas compressor in combination. The weights of all other components in this scenario are independent of the selection of product flow rate, product purity, product delivery pressure, and system run time. The total weight of the oxygen concentrator system thus may be minimized by selecting PVSA operating conditions that minimize the weight of the variable-weight components.

The embodiments of the present invention are directed to methods for minimizing the weight of the variable-weight components by optimizing PVSA operating conditions as described below. Reducing the weight of the fixed-weight components (i.e., those components whose weights are essentially independent of PVSA cycle operating conditions) may be possible by improvements in materials, motor design, electrical systems, and the like, but these are not addressed by embodiments of the present invention.

The adsorbent weight requirement may be determined by the amount of adsorbent required to remove the nitrogen from feed air such that a desired oxygen product purity is attained. The adsorbent weight requirement can be determined by the relation $$W_a = \frac{n_{ads}}{n} * \frac{1}{B}$$

where $n_{ads}$ is the moles of nitrogen to be removed per minute, n is the nitrogen working capacity in moles of nitrogen adsorbed by the adsorbent in one adsorber bed during one bed cycle, and B is the rate at which a fresh adsorber bed is available for feed in beds/min and is determined by the PVSA cycle time. The parameter $n_{ads}$ can be determined by:

$$n_{ads} = \frac{Q_p y_{O2,p} y_{N2,f}}{\theta_{O2} y_{O2,f}}$$

where $Q_p$ is the product flow in moles per minute, $y_{O2,p}$ is the product purity in percent oxygen, $y_{N2,\theta}$ is the nitrogen concentration in the feed in percent, $\theta_{O2}$ is the oxygen recovery in per cent (i.e., the percent of the oxygen in the feed gas that is present in the product gas), and $y_{O2,f}$ is the oxygen concentration in the feed in percent. The nitrogen working capacity of the adsorbent is dependent on the pressure envelope to which the adsorbent is exposed. The preferred method to determine adsorbent working capacity is to measure oxygen and nitrogen pure component isotherms at multiple temperatures from which parameters can be determined by the application of the dual site Langmuir model [see Myers, A. L., Activity Coefficients of Mixtures Adsorbed on Heterogeneous Surfaces, *AIChE J.* 1983 (29), 691]

$$n_i = \frac{M_1 bp}{1+bp} + \frac{M_2 dp}{1+dp}$$

where $M_1$, b, $M_2$, and d are fit parameters and p is pressure. The Langmuir model then is used to determine working capacity by means of multicomponent adsorption models, namely the ideal adsorption solution theory (IAST) [see Myers, A. L. and Prausnitz, J. M., Thermodynamics of Mixed Gas Adsorption, *AIChE J.* 1965 (1), 11] or more preferably the heterogeneous ideal adsorbed solution theory (HIAST) [see Mathias P. M. et al, Correlation of Multicomponent Gas Adsorption by the Dual-Site Langmuir Model. Application to Nitrogen/Oxygen Adsorption on 5A Zeolite, *Ind. & Eng. Chem Res.* 1996 (35), 7].

The weight of the primary gas mover (i.e., the combined weight of the feed air compressor and the vacuum waste gas compressor), $W_p$, may be determined based on requirements of the two compressors to provide gas at the specified pressures during the feed step of the cycle and the required flow rate during the vacuum and purge steps of the cycle. The weight of the primary gas mover will vary based on the geometry of the compressor; for example, the size of the involutes in a scroll compressor will vary based on the gas compression ratio. The weight of the primary gas mover does not include the electric motor which powers the primary gas mover and is considered a fixed weight for the present analysis, wherein the motor can be operated at various speeds depending on the required feed gas and waste gas compression duty. The weight of the primary gas mover is determined to be proportional to the oxygen production rate for the present analysis. The weight of the rechargeable power supply, in this case a battery, may be optimized by applying the relationship of energy discharge to the requirements over the duration of the PVSA cycle. The power supplied by the battery to the other components of the oxygen generator (alarms, valve motor, etc) may be about 5 W. The power required from the battery to operate the feed air compressor and the vacuum waste gas compressor may be determined directly by the adiabatic power of compression based on the pressures used during the PVSA cycles. Adiabatic power is given by the expression $$P_{ad} = \frac{\dot{m}kRT_1}{k-1}\left[\left(\frac{p_2}{p_1}\right)^{\left(\frac{k-1}{k}\right)} - 1\right]$$

where $\dot{m}$ is the mass flow rate, R is the gas constant, $T_1$ is the temperature of the inlet gas, $p_2$ is the pressure of the outlet gas, $p_1$ is the pressure of the inlet gas to the compressor, and k is the ratio of heat capacity at constant pressure to heat capacity at constant volume and equals 1.4 for air. When operating in the compression mode, $p_2$ is the air feed pressure and $p_1$ is atmospheric pressure. When operating in the vacuum mode, $p_2$ is atmospheric pressure and $p_1$ is the waste gas pressure exiting the adsorbent bed.

The battery power density may be determined from manufacturers' specifications. For a state-of-the-art lithium ion battery, for example, the energy density $\rho_{batt}$ is given in lb/Wh. For any given run time, $t_r$ (in hours), the weight of the battery (in pounds) may be described by the relation $$W_b = \frac{\rho_{batt} P_{ad} t_r}{\eta_p \eta_m}$$

where $\eta_p$ and $\eta_m$ are the efficiencies of the compressors and the drive motor, respectively.

The overall weight of the variable-weight components may be determined from the relationship of each individual component weight to the characteristics of the cycle, specifically the operating pressure envelope. The total weight of the variable-weight components therefore is a function of the minimum pressure during evacuation, $p_{min}$, and the product pressure, $p_{prod}$.

The desirable weight of the variable components may be determined by first selecting a product flow rate, product pressure, and run time. Then, using the total weight function, the combined weight of all three components can be plotted as a function of a single variable, the minimum bed pressure, as given below:

$$W_t = \{W_a + W_p + W_b\}(p_{min})$$

The desirable weight of the variable components is determined by first selecting a product flow rate, product pressure, and run time. Then, using the total weight function, the combined weight of all three components can be plotted as a function of a single variable, the minimum bed pressure. Plotting the weight of the variable-weight components vs. the minimum bed pressure at constant production rate, product purity, product pressure, and run time shows unexpectedly that there is a minimum pressure, or a range of desirable minimum pressures, that correspond to a minimum weight or range of desirable minimum weights of the variable-weight components.

The following Examples illustrate this feature but do not limit the embodiments of the invention to any of the specific details described therein. Each of the Examples is based on providing a product containing 93 mole % oxygen at various delivery pressures, flow rates, and run times using (a) the five bed PVSA system of FIG. 1 with the PVSA cycle described in Tables 1 and 2, and (b) a four bed PVSA system with the cycle described in Tables 3 and 4. The adsorbent is a sodium- and lithium-exchanged low-silica X-type zeolite (LSX) in bead form with an average particle diameter of 0.50 mm. In calculating the weight of the adsorbent required using the nitrogen adsorption equations given above, a bed utilization factor of 70% was used to account for the fact that 70% of the adsorbent capacity is utilized for nitrogen adsorption while the remaining 30% of the adsorbent capacity is utilized for the adsorption of water and carbon dioxide.

The efficiency of drive motor 13 in primary gas mover 11 typically may be 80% and the efficiency of compressors 9 and 15 typically may be 70%. The system is powered by a rechargeable lithium ion battery such as, for example, one manufactured and sold by Varta having a fixed energy density of 12.46 lb/kWh per the manufacturer's specifications. The total weight of the system is the sum of the weight of the fixed-weight components (housing, tubing, electrical wiring, etc) and the variable weights of the adsorbent, the primary gas mover (i.e., the feed air compressor and the vacuum waste gas compressor), and the battery.

EXAMPLE 1

Figure 2:
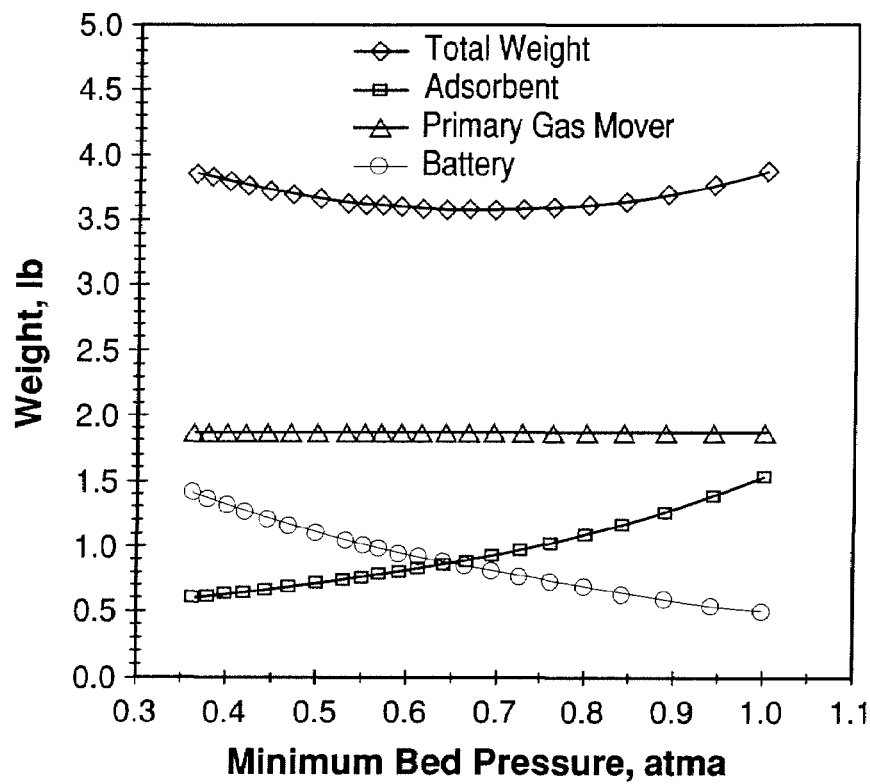
FIG. 2 is a plot of individual component variable weights and total component variable weight vs. minimum bed pressure for a five bed PVSA system illustrating a first embodiment of the invention.

A PVSA system was simulated to generate 3 lpm of 93 mole % oxygen at a product pressure of 1.6 atm for a period of 1 hour of continuous run time for a five-bed system of FIG. 1 using the cycle of Tables 1 and 2. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.35 and 1.0 atma. These weights were summed and all data were plotted as shown in FIG. 2. The three individual component weights show no obvious minima as functions of the minimum bed pressure. When these weights are combined, however, the plot of total variable weight vs. minimum bed pressure exhibits a minimum total variable weight of 3.6 lb at 0.7 atma. A desirable relative weight range between the minimum weight and 5% above the minimum weight was defined to yield a desirable total variable weight range of 3.6 to 3.8 lb. This corresponds to a range of the minimum bed pressure of 0.4 to 0.9 atma, which is a desirable PVSA operating range for this Example. In this desirable pressure range, the weight of the adsorbent is between a lower value of 0.7 lb and an upper value of 1.4 lb, the weight of the primary gas mover is 1.9 lb, and the weight of the battery is between a lower value of 0.5 lb and an upper value of 1.2 lb.

EXAMPLE 2

Figure 3:
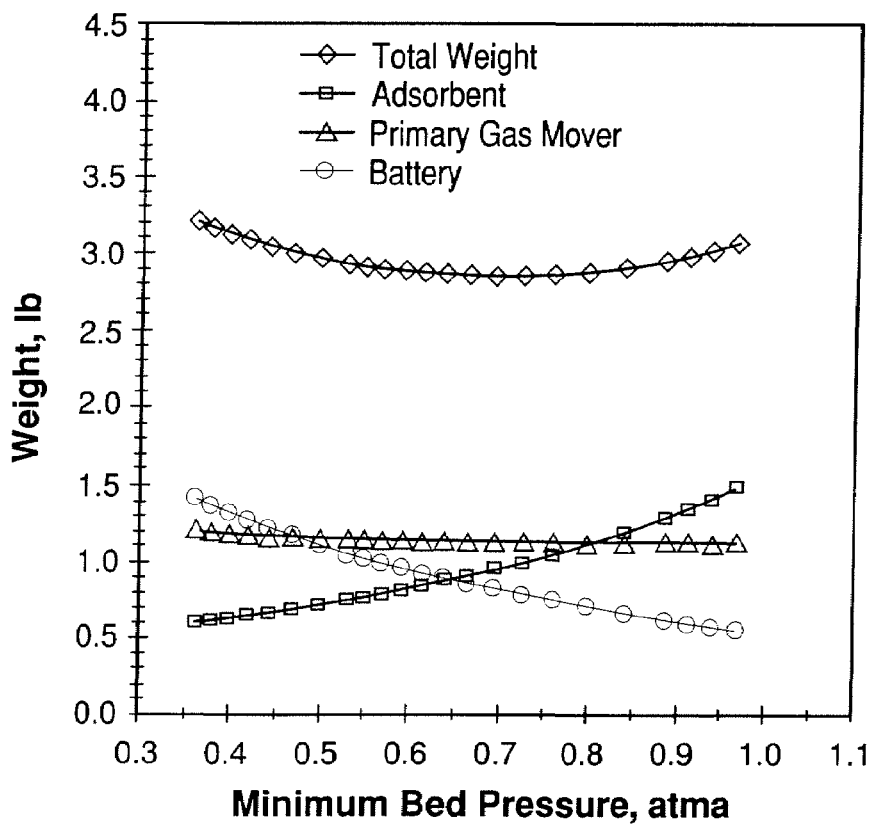
FIG. 3 is a plot of individual component variable weights and total component variable weight vs. minimum bed pressure for a five bed PVSA system illustrating a second embodiment of the invention.

Example 1 was repeated using a primary gas mover consisting of diaphragm-type feed air and waste gas compressors driven by a common motor. The weight of each variable-weight component, i.e., the adsorbent, primary gas mover, and battery, were calculated using the methods described earlier for values of the minimum bed pressure between 0.35 and 0.96 atma. These weights were summed and all data were plotted as shown in FIG. 3. The three individual component weights show no obvious minima as functions of the minimum bed pressure. When these weights are combined, however, the plot of total variable weight vs. minimum bed pressure exhibits a minimum total variable weight of 2.8 lb at about 0.7 atma. A desirable relative weight range between the minimum weight and 5% above the minimum weight was defined to yield a desirable total variable weight range of 2.8 to 3.0 lb. This corresponds to a range of the minimum bed pressure of 0.5 to 0.9 atma, which is a desirable PVSA operating range for this Example. In this desirable pressure range, the weight of the adsorbent is between a lower value of 0.7 lb and an upper value of 1.3 lb, the weight of the primary gas mover is 1.1 lb, and the weight of the battery is between a lower value of 0.6 lb and an upper value of 1.1 lb.

EXAMPLE 3

Figure 4:
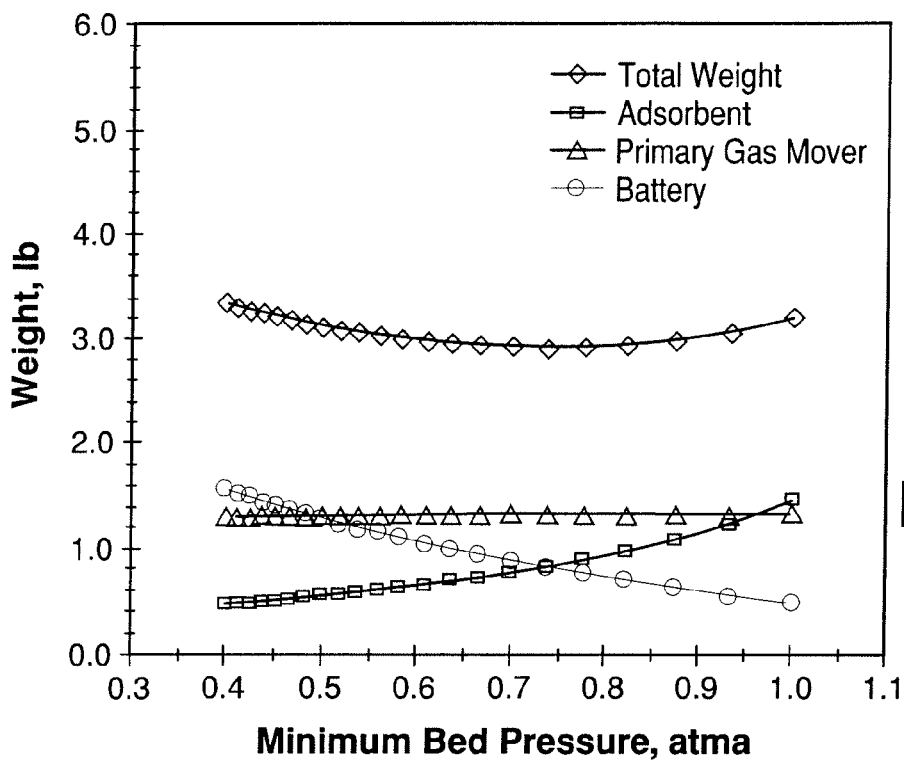
FIG. 4 is a plot of individual component variable weights and total component variable weight vs. minimum bed pressure for a five bed PVSA system illustrating a third embodiment of the invention.

A PVSA system was simulated to generate 2 lpm of 93 mole % oxygen at a product pressure of 1.4 atm for a period of 2 hours of continuous run time for a five-bed system of FIG. 1 using the cycle of Tables 1 and 2. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.4 and 1.0 atma. These weights were summed and all data were plotted as shown in FIG. 4. The three individual component weights show no obvious minima as functions of the minimum bed pressure. When these weights are combined, however, the plot of total variable weight vs. minimum bed pressure exhibits a minimum total variable weight of 2.9 lb at 0.7 atma. A desirable relative weight range between the minimum weight and 5% above the minimum weight was defined to yield a desirable total variable weight range of 2.9 to 3.1 lb. This corresponds to a range of the minimum bed pressure of about 0.6 to about 0.9 atma, which is a desirable PVSA operating range for this Example. In this desirable pressure range, the weight of the adsorbent is between a lower value of 0.6 lb and an upper value of 1.2 lb, the weight of the primary gas mover is 1.3 lb, and the weight of the battery is between a lower value of 0.5 lb and an upper value of 1.1 lb.

EXAMPLE 4

Figure 5:
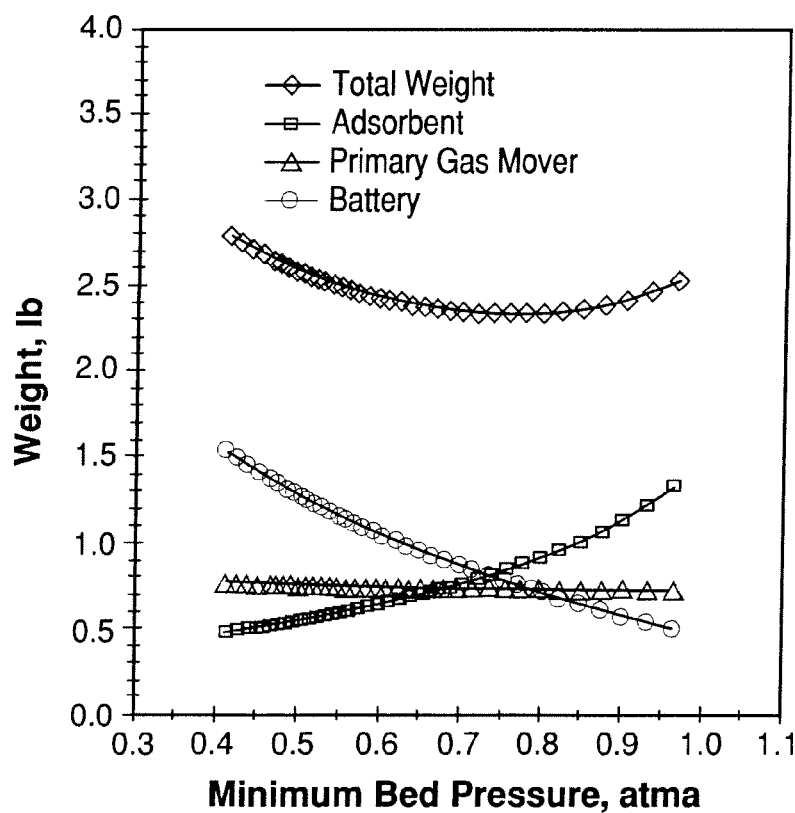
FIG. 5 is a plot of individual component variable weights and total component variable weight vs. minimum bed pressure for a five bed PVSA system illustrating a fourth embodiment of the invention.

Example 3 was repeated using a primary gas mover consisting of diaphragm-type feed air and waste gas compressors driven by a common motor. The weight of each variable-weight component, i.e., the adsorbent, primary gas mover, and battery, were calculated using the methods described earlier for values of the minimum bed pressure between 0.40 and 0.96 atma. These weights were summed and all data were plotted as shown in FIG. 5. The three individual component weights show no obvious minima as functions of the minimum bed pressure. When these weights are combined, however, the plot of total variable weight vs. minimum bed pressure exhibits a minimum total variable weight of 2.3 lb at about 0.8 atma. A desirable relative weight range between the minimum weight and 5% above the minimum weight was defined to yield a desirable total variable weight range of 2.3 to 2.5 lb. This corresponds to a range of the minimum bed pressure of 0.6 to about 0.9 atma, which is a desirable PVSA operating range for this Example. In this desirable pressure range, the weight of the adsorbent is between a lower value of 0.6 lb and an upper value of 1.1 lb, the weight of the primary gas mover is 0.7 lb, and the weight of the battery is between a lower value of 0.6 lb and an upper value of 1.1 lb.

EXAMPLE 5

Figure 6:
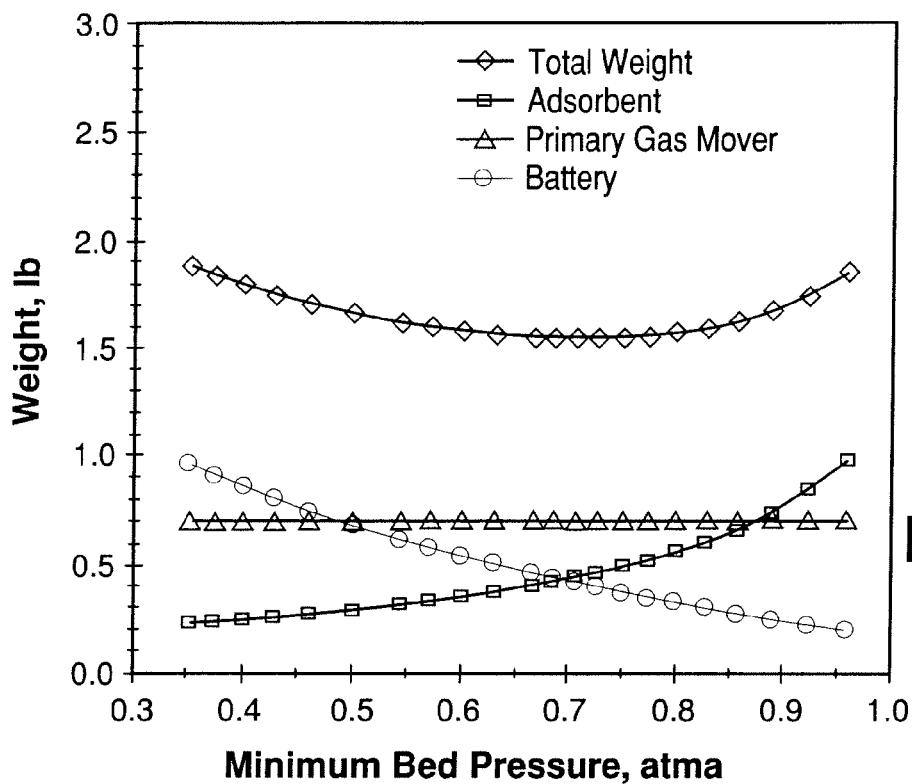
FIG. 6 is a plot of individual component variable weights and total component variable weight vs. minimum bed pressure for a five bed PVSA system illustrating a fifth embodiment of the invention.

A PVSA system was simulated to generate 1 lpm of 93 mole % oxygen at a product pressure of 1.2 atm for a period of 3 hours of continuous run time for a five-bed system of FIG. 1 using the cycle of Tables 1 and 2. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.35 and 0.96 atma. These weights were summed and all data were plotted as shown in FIG. 6. The three individual component weights show no obvious minima as functions of the minimum bed pressure. When these weights are combined, however, the plot of total variable weight vs. minimum bed pressure exhibits a minimum total variable weight of 1.5 lb at about 0.7 atma. A desirable relative weight range between the minimum weight and 5% above the minimum weight was defined to yield a desirable total variable weight range of 1.5 to 1.6 lb. This corresponds to a range of the minimum bed pressure of about 0.6 to 0.8 atma, which is a desirable PVSA operating range for this Example. In this desirable pressure range, the weight of the adsorbent is between a lower value of 0.3 lb and an upper value of 0.6 lb, the weight of the primary gas mover is 0.7 lb, and the weight of the battery is between a lower value of 0.3 lb and an upper value of 0.6 lb.

EXAMPLE 6

Figure 7:
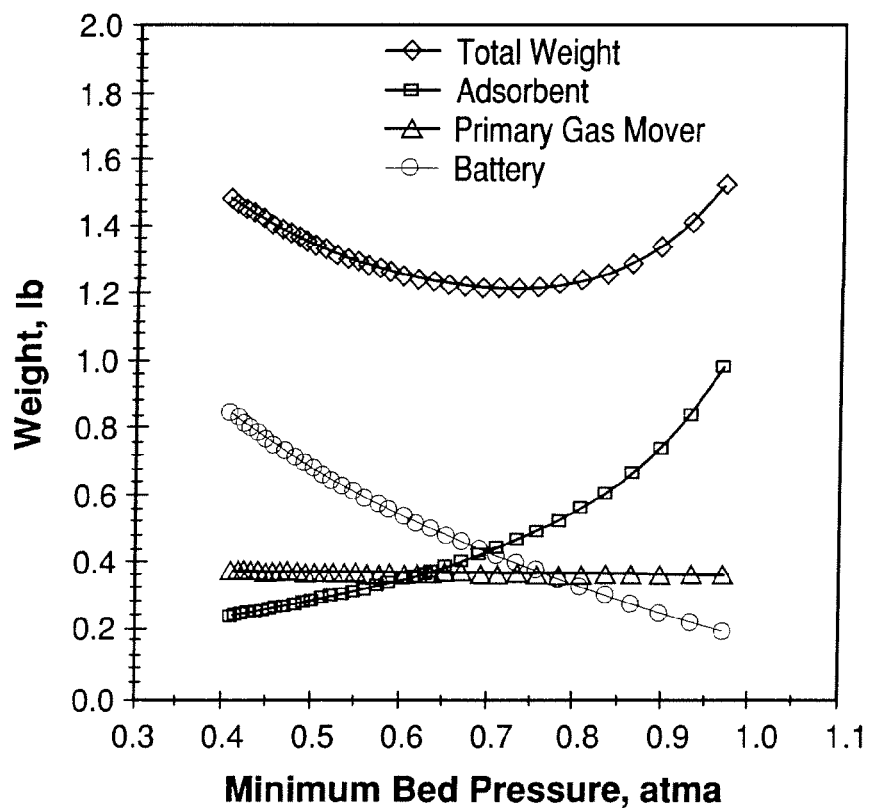
FIG. 7 is a plot of individual component variable weights and total component variable weight vs. minimum bed pressure for a five bed PVSA system illustrating a sixth embodiment of the invention.

Example 5 was repeated using a primary gas mover consisting of diaphragm-type feed air and waste gas compressors driven by a common motor. The weight of each variable-weight component, i.e., the adsorbent, primary gas mover, and battery, were calculated using the methods described earlier for values of the minimum bed pressure between 0.40 and 0.96 atma. These weights were summed and all data were plotted as shown in FIG. 7. The three individual component weights show no obvious minima as functions of the minimum bed pressure. When these weights are combined, however, the plot of total variable weight vs. minimum bed pressure exhibits a minimum total variable weight of 1.3 lb at about 0.7 atma. A desirable relative weight range between the minimum weight and 5% above the minimum weight was defined to yield a desirable total variable weight range of 1.2 to 1.3 lb. This corresponds to a range of the minimum bed pressure of 0.6 to about 0.8 atma, which is a desirable PVSA operating range for this Example. In this desirable pressure range, the weight of the adsorbent is between a lower value of 0.3 lb and an upper value of 0.6 lb, the weight of the primary gas mover is 0.4 lb, and the weight of the battery is between a lower value of 0.3 lb and an upper value of 0.6 lb.

EXAMPLE 7

Figure 8:
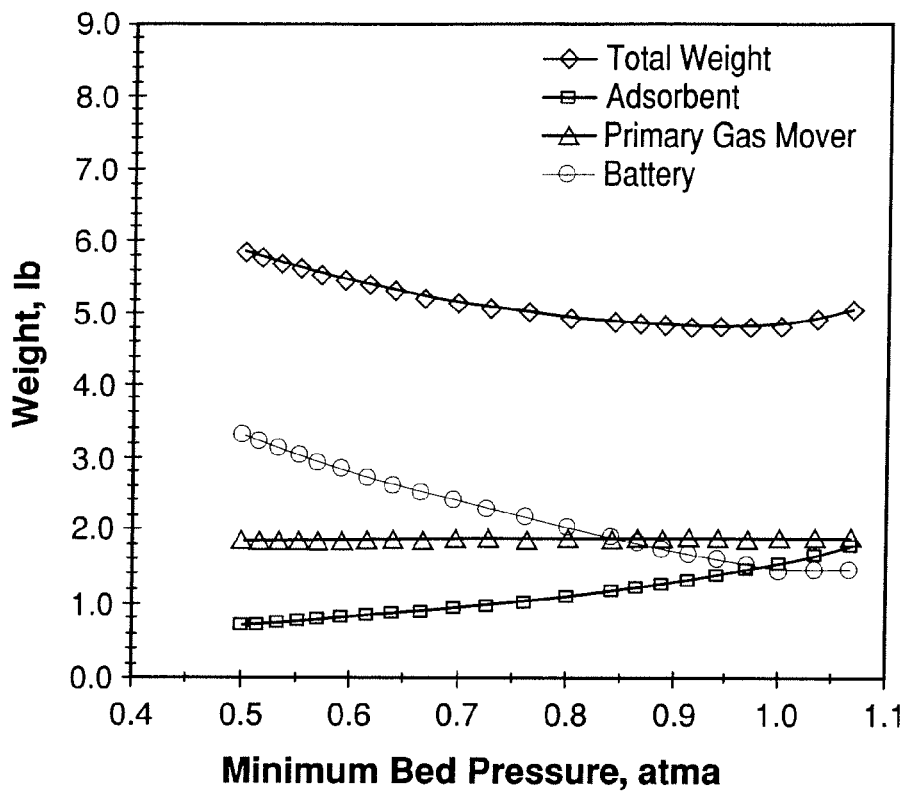
FIG. 8 is a plot of individual component variable weights and total component variable weight vs. minimum bed pressure for a five bed PVSA system illustrating a seventh embodiment of the invention.

A PVSA system was simulated to generate 3 lpm of 93 mole % oxygen at a product pressure of 1.6 atm for a period of 3 hours of continuous run time for a five-bed system of FIG. 1 using the cycle of Tables 1 and 2. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.5 and 1.06 atma. These weights were summed and all data were plotted as shown in FIG. 8. The three individual component weights show no obvious minima as functions of the minimum bed pressure. When these weights are combined, however, the plot of total variable weight vs. minimum bed pressure exhibits a minimum total variable weight of 4.8 lb at about 0.9 atma. A desirable relative weight range between the minimum weight and 5% above the minimum weight was defined to yield a desirable total variable weight range of 4.8 to 5.0 lb. This corresponds to a range of the minimum bed pressure of about 0.8 to 1.1 atma, which is a desirable PVSA operating range for this Example. In this desirable pressure range, the weight of the adsorbent is between a lower value of 1.0 lb and an upper value of 1.8 lb, the weight of the primary gas mover is 1.9 lb, and the weight of the battery is between a lower value of 1.4 lb and an upper value of 2.1 lb.

EXAMPLE 8

Figure 9:
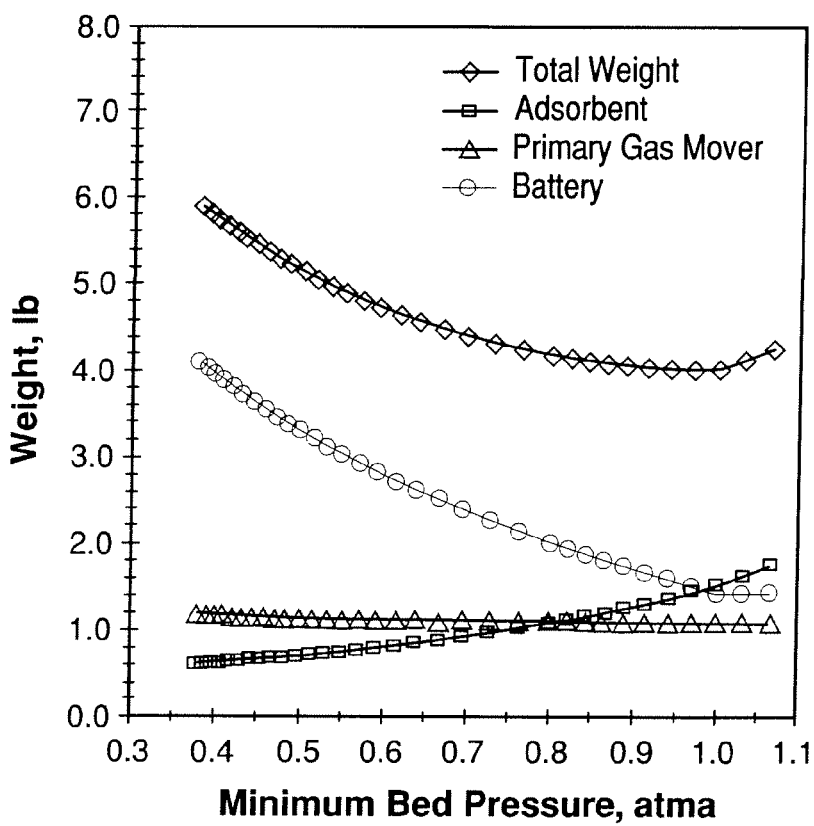
FIG. 9 is a plot of individual component variable weights and total component variable weight vs. minimum bed pressure for a five bed PVSA system illustrating an eighth embodiment of the invention.

Example 7 was repeated using a primary gas mover consisting of diaphragm-type feed air and waste gas compressors driven by a common motor. The weight of each variable-weight component, i.e., the adsorbent, primary gas mover, and battery, were calculated using the methods described earlier for values of the minimum bed pressure between 0.37 and 1.06 atma. These weights were summed and all data were plotted as shown in FIG. 9. The three individual component weights show no obvious minima as functions of the minimum bed pressure. When these weights are combined, however, the plot of total variable weight vs. minimum bed pressure exhibits a minimum total variable weight of 4.0 lb at about 0.9 atma. A desirable relative weight range between the minimum weight and 5% above the minimum weight was defined to yield a desirable total variable weight range of 4.0 to 4.2 lb. This corresponds to a range of the minimum bed pressure of 0.8 to about 1.0 atma, which is a desirable PVSA operating range for this Example. In this desirable pressure range, the weight of the adsorbent is between a lower value of 1.1 lb and an upper value of 1.6 lb, the weight of the primary gas mover is 1.1 lb, and the weight of the battery is between a lower value of 1.4 lb and an upper value of 2.0 lb.

EXAMPLE 9

Figure 10:
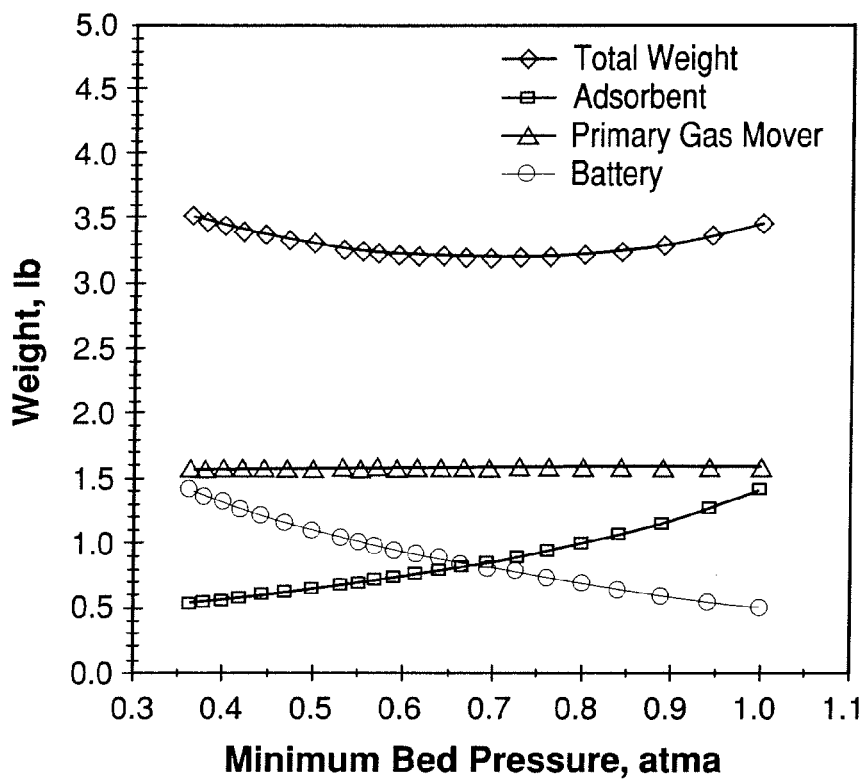
FIG. 10 is a plot of individual component variable weights and total component variable weight vs. minimum bed pressure for a four bed PVSA system illustrating a first alternative embodiment of the invention.

Example 1 was repeated except that the PVSA system was a four bed system operated according to the cycle of Tables 3 and 4. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.35 and 1.0 atma. These weights were summed and all data were plotted as shown in FIG. 10. The three individual component weights show no obvious minima as functions of the minimum bed pressure. When these weights are combined, however, the plot of total variable weight vs. minimum bed pressure exhibits a minimum total variable weight of 3.2 lb at 0.7 atma. A desirable relative weight range between the minimum weight and 5% above the minimum weight was defined to yield a desirable total variable weight range of 3.2 to 3.4 lb. This corresponds to a range of the minimum bed pressure of 0.5 to about 0.9 atma, which is a desirable PVSA operating range for this Example. In this desirable pressure range, the weight of the adsorbent is between a lower value of 0.6 lb and an upper value of 1.3 lb, the weight of the primary gas mover is 1.6 lb, and the weight of the battery is between a lower value of 0.5 lb and an upper value of 1.2 lb.

EXAMPLE 10

Figure 11:
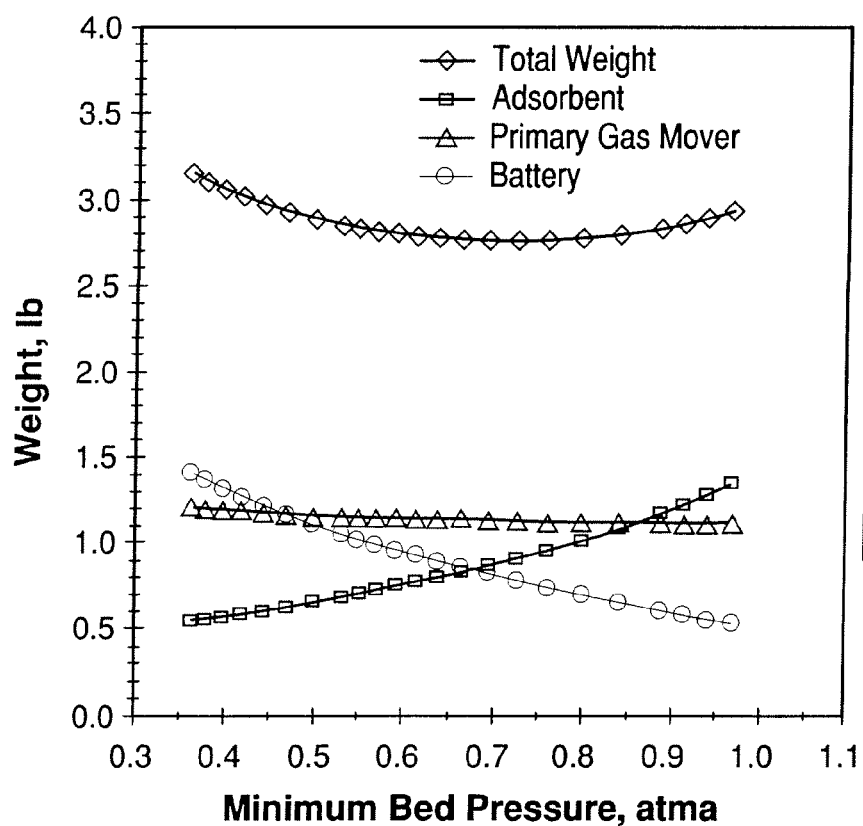
FIG. 11 is a plot of individual component variable weights and total component variable weight vs. minimum bed pressure for a four bed PVSA system illustrating a second alternative embodiment of the invention.

Example 2 was repeated except that the PVSA system was a four bed system operated according to the cycle of Tables 3 and 4. The primary gas mover consisted of diaphragm-type feed air and waste gas compressors driven by a common motor. The weight of each variable-weight component, i.e., the adsorbent, primary gas mover, and battery, were calculated using the methods described earlier for values of the minimum bed pressure between 0.35 and 0.96 atma. These weights were summed and all data were plotted as shown in FIG. 11. The three individual component weights show no obvious minima as functions of the minimum bed pressure. When these weights are combined, however, the plot of total variable weight vs. minimum bed pressure exhibits a minimum total variable weight of 2.7 lb at 0.7 atma. A desirable relative weight range between the minimum weight and 5% above the minimum weight was defined to yield a desirable total variable weight range of 2.7 to 2.9 lb. This corresponds to a range of the minimum bed pressure of about 0.5 to 0.9 atma, which is a desirable PVSA operating range for this Example. In this desirable pressure range, the weight of the adsorbent is between a lower value of 0.7 lb and an upper value of 1.3 lb, the weight of the primary gas mover is 1.1 lb, and the weight of the battery is between a lower value of 0.5 lb and an upper value of 1.0 lb.

EXAMPLE 11

Figure 12:
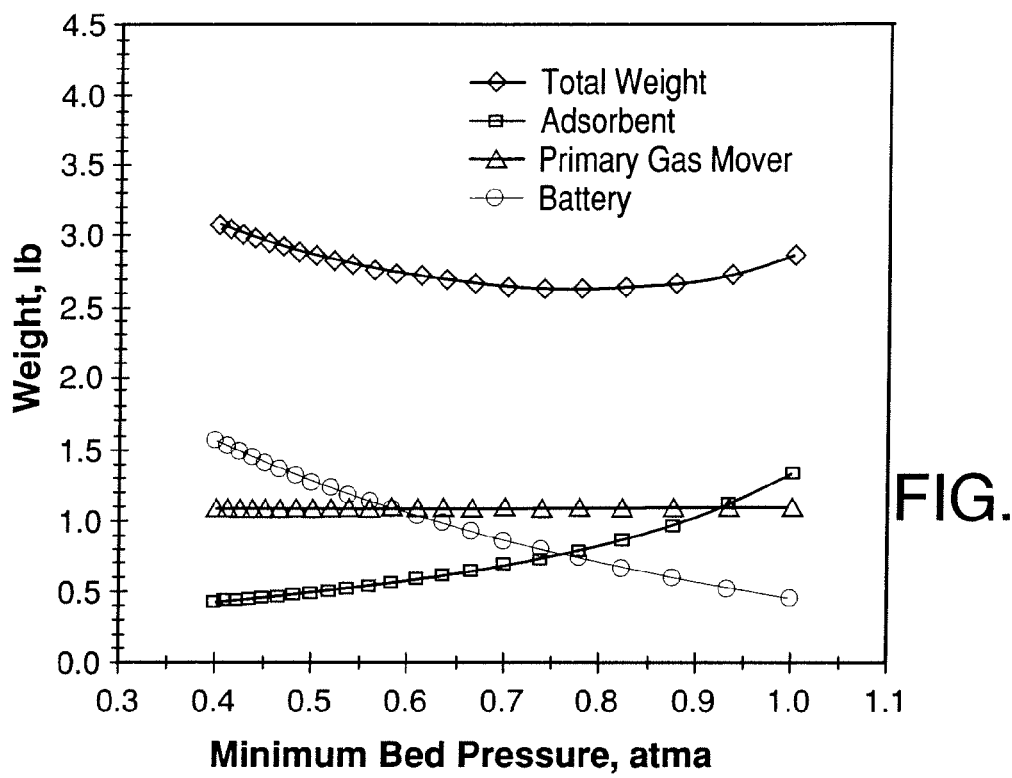
FIG. 12 is a plot of individual component variable weights and total component variable weight vs. minimum bed pressure for a four bed PVSA system illustrating a third alternative embodiment of the invention.

Example 3 was repeated except that the PVSA system was a four bed system operated according to the cycle of Tables 3 and 4. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.4 and 1.0 atma. These weights were summed and all data were plotted as shown in FIG. 12. The three individual component weights show no obvious minima as functions of the minimum bed pressure. When these weights are combined, however, the plot of total variable weight vs. minimum bed pressure exhibits a minimum total variable weight of 2.6 lb at 0.8 atma. A desirable relative weight range between the minimum weight and 5% above the minimum weight was defined to yield a desirable total variable weight range of 2.6 to 2.8 lb. This corresponds to a range of the minimum bed pressure of 0.6 to about 0.9 atma, which is a desirable PVSA operating range for this Example. In this desirable pressure range, the weight of the adsorbent is between a lower value of 0.6 lb and an upper value of 1.1 lb, the weight of the primary gas mover is 1.1 lb, and the weight of the battery is between a lower value of 0.5 lb and an upper value of 1.1 lb.

EXAMPLE 12

Figure 13:
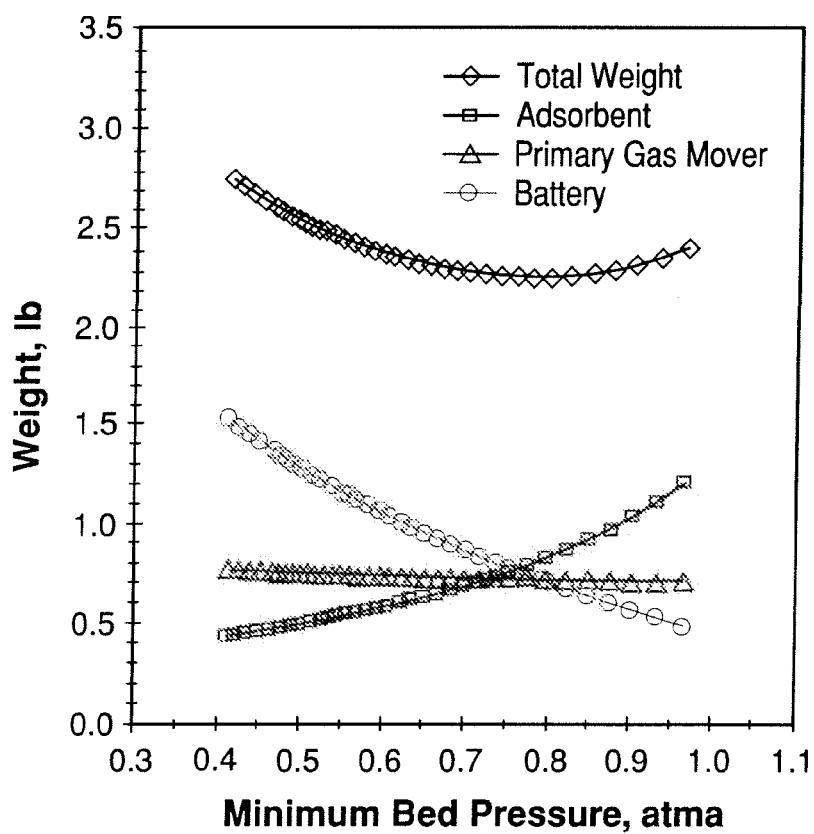
FIG. 13 is a plot of individual component variable weights and total component variable weight vs. minimum bed pressure for a four bed PVSA system illustrating a fourth alternative embodiment of the invention.

Example 4 was repeated except that the PVSA system was a four bed system operated according to the cycle of Tables 3 and 4. The primary gas mover consisted of diaphragm-type feed air and waste gas compressors driven by a common motor. The weight of each variable-weight component, i.e., the adsorbent, primary gas mover, and battery, were calculated using the methods described earlier for values of the minimum bed pressure between 0.4 and 0.96 atma. These weights were summed and all data were plotted as shown in FIG. 13. The three individual component weights show no obvious minima as functions of the minimum bed pressure. When these weights are combined, however, the plot of total variable weight vs. minimum bed pressure exhibits a minimum total variable weight of 2.3 lb at about 0.8 atma. A desirable relative weight range between the minimum weight and 5% above the minimum weight was defined to yield a desirable total variable weight range of 2.3 to 2.4 lb. This corresponds to a range of the minimum bed pressure of about 0.6 to about 0.9 atma, which is a desirable PVSA operating range for this Example. In this desirable pressure range, the weight of the adsorbent is between a lower value of 0.6 lb and an upper value of 1.1 lb, the weight of the primary gas mover is 0.7 lb, and the weight of the battery is between a lower value of 0.5 lb and an upper value of 1.0 lb.

EXAMPLE 13

Figure 14:
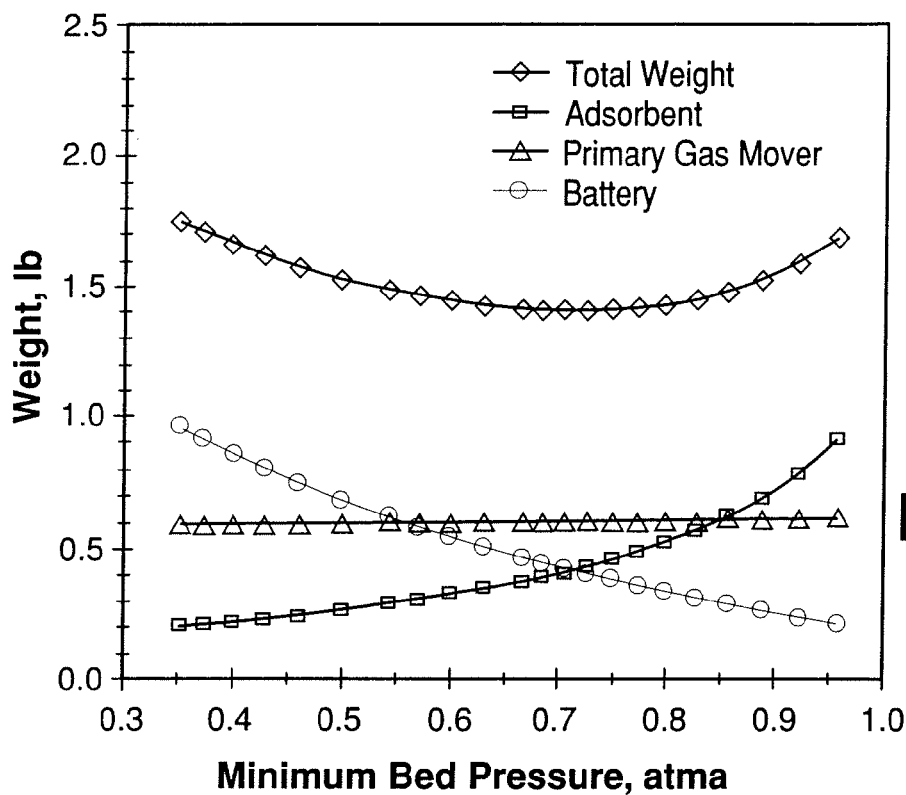
FIG. 14 is a plot of individual component variable weights and total component variable weight vs. minimum bed pressure for a four bed PVSA system illustrating a fifth alternative embodiment of the invention.

Example 5 was repeated except that the PVSA system was a four bed system operated according to the cycle of Tables 3 and 4. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.35 and 0.96 atma. These weights were summed and all data were plotted as shown in FIG. 14. The three individual component weights show no obvious minima as functions of the minimum bed pressure. When these weights are combined, however, the plot of total variable weight vs. minimum bed pressure exhibits a minimum total variable weight of 1.4 lb at about 0.7 atma. A desirable relative weight range between the minimum weight and 5% above the minimum weight was defined to yield a desirable total variable weight range of 1.4 to 1.5 lb. This corresponds to a range of the minimum bed pressure of 0.6 to 0.9 atma, which is a desirable PVSA operating range for this Example. In this desirable pressure range, the weight of the adsorbent is between a lower value of 0.3 lb and an upper value of 0.6 lb, the weight of the primary gas mover is 0.6 lb, and the weight of the battery is between a lower value of 0.3 lb and an upper value of 0.5 lb.

EXAMPLE 14

Figure 15:
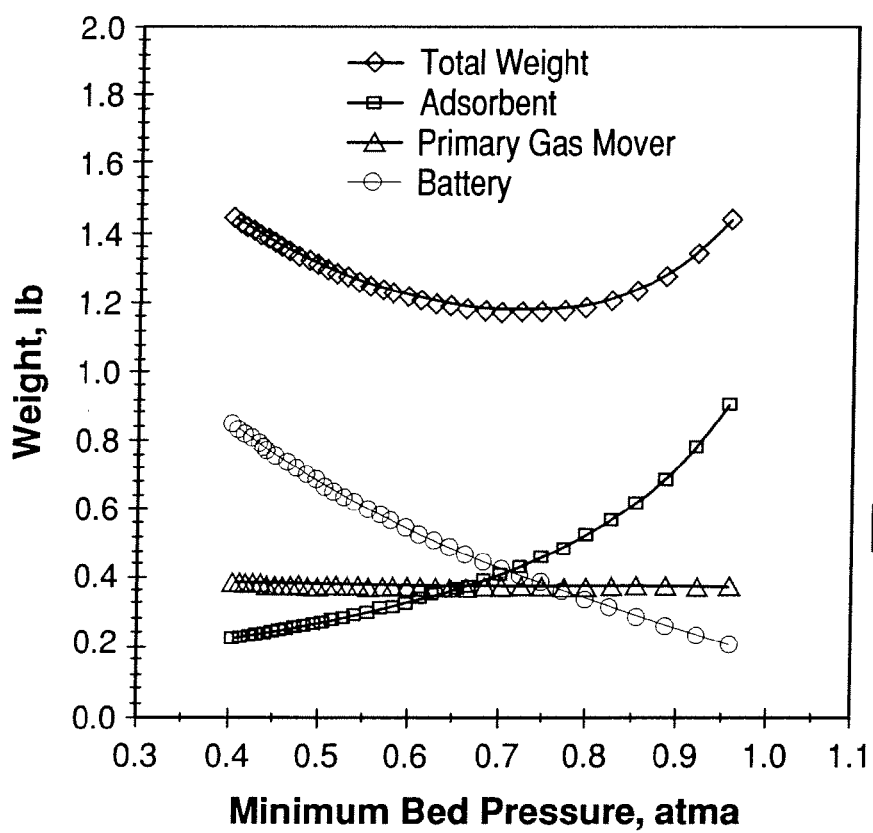
FIG. 15 is a plot of individual component variable weights and total component variable weight vs. minimum bed pressure for a four bed PVSA system illustrating a sixth alternative embodiment of the invention.

Example 6 was repeated except that the PVSA system was a four bed system operated according to the cycle of Tables 3 and 4. The primary gas mover consisted of diaphragm-type feed air and waste gas compressors driven by a common motor. The weight of each variable-weight component, i.e., the adsorbent, primary gas mover, and battery, were calculated using the methods described earlier for values of the minimum bed pressure between 0.4 and 0.96 atma. These weights were summed and all data were plotted as shown in FIG. 15. The three individual component weights show no obvious minima as functions of the minimum bed pressure. When these weights are combined, however, the plot of total variable weight vs. minimum bed pressure exhibits a minimum total variable weight of 1.2 lb in a range of the minimum bed pressure of about 0.6 to 0.8 atma, which is a desirable PVSA operating range for this Example. In this desirable pressure range, the weight of the adsorbent is between a lower value of 0.3 lb and an upper value of 0.6 lb, the weight of the primary gas mover is 0.4 lb, and the weight of the battery is between a lower value of 0.3 lb and an upper value of 0.5 lb.

EXAMPLE 15

Figure 16:
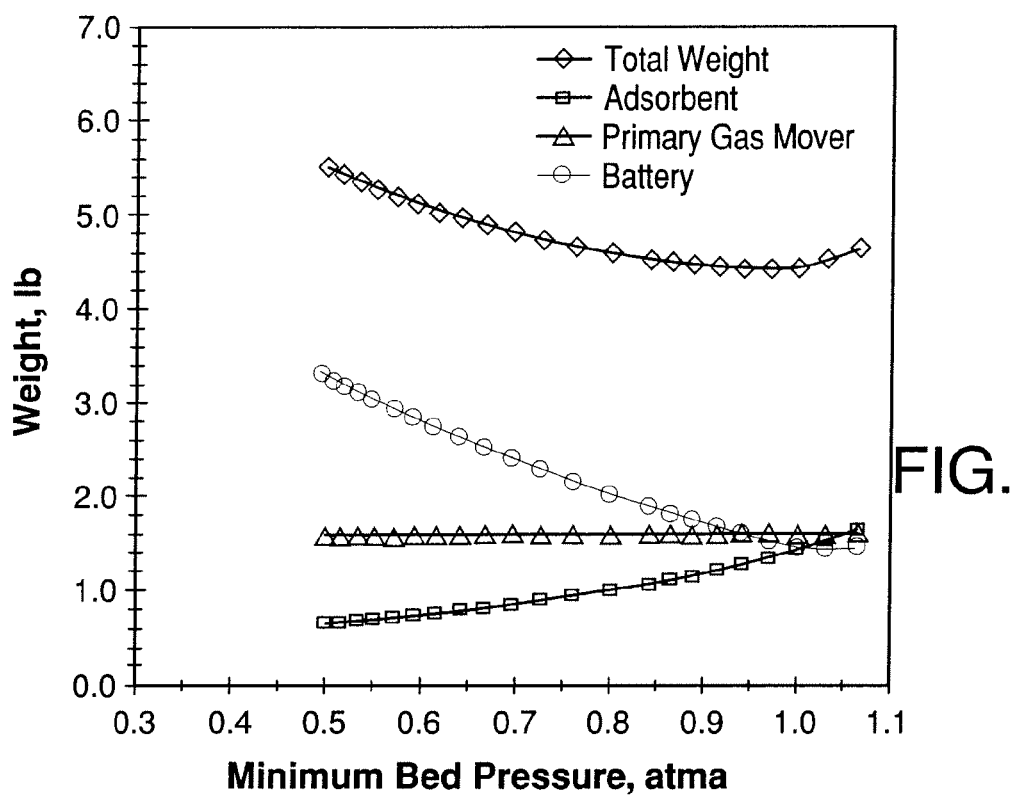
FIG. 16 is a plot of individual component variable weights and total component variable weight vs. minimum bed pressure for a four bed PVSA system illustrating a seventh alternative embodiment of the invention.

Example 7 was repeated except that the PVSA system was a four bed system operated according to the cycle of Tables 3 and 4. The primary gas mover consisted of scroll-type feed air and waste gas compressors driven by a common motor. The weight of each variable-weight component, i.e., the adsorbent, primary gas mover, and battery, were calculated using the methods described earlier for values of the minimum bed pressure between 0.5 and 1.06 atma. These weights were summed and all data were plotted as shown in FIG. 16. The three individual component weights show no obvious minima as functions of the minimum bed pressure. When these weights are combined, however, the plot of total variable weight vs. minimum bed pressure exhibits a minimum total variable weight of 4.4 lb at slightly below 1.0 atma. A desirable relative weight range between the minimum weight and 5% above the minimum weight was defined to yield a desirable total variable weight range of 4.4 to 4.6 lb. This corresponds to a range of the minimum bed pressure of about 0.8 to 1.1 atma, which is a desirable PVSA operating range for this Example. In this desirable pressure range, the weight of the adsorbent is between a lower value of 1.0 lb and an upper value of 1.6 lb, the weight of the primary gas mover is 1.6 lb, and the weight of the battery is between a lower value of 1.4 lb and an upper value of 2.0 lb.

EXAMPLE 16

Figure 17:
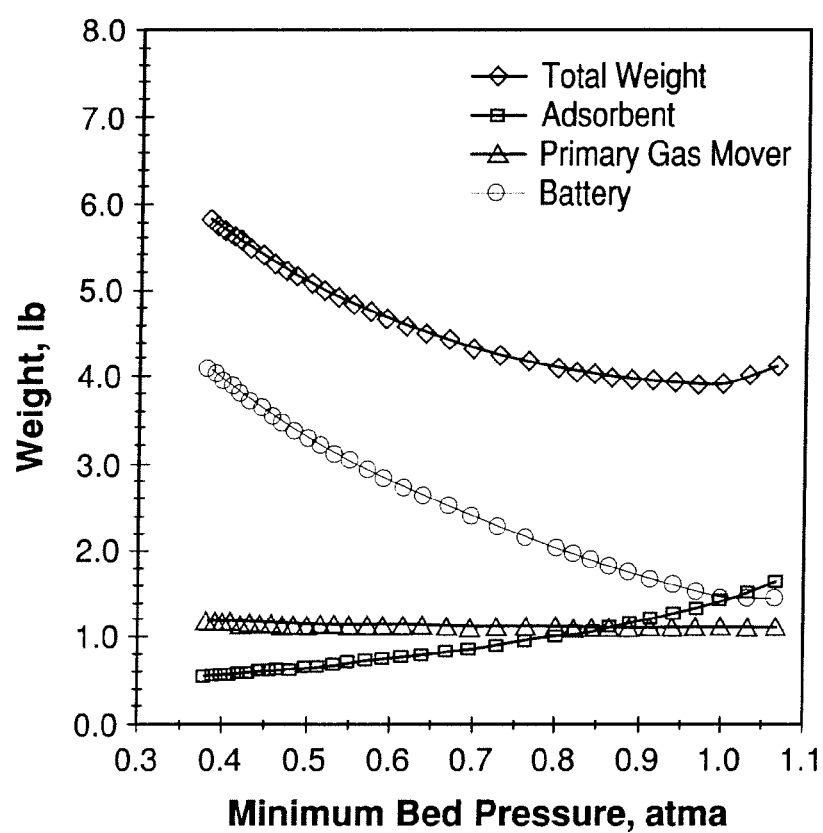
FIG. 17 is a plot of individual component variable weights and total component variable weight vs. minimum bed pressure for a four bed PVSA system illustrating an eighth alternative embodiment of the invention.

Example 8 was repeated except that the PVSA system was a four bed system operated according to the cycle of Tables 3 and 4. The primary gas mover consisted of diaphragm-type feed air and waste gas compressors driven by a common motor. The weight of each variable-weight component, i.e., the adsorbent, primary gas mover, and battery, were calculated using the methods described earlier for values of the minimum bed pressure between about 0.37 and 1.06 atma. These weights were summed and all data were plotted as shown in FIG. 17. The three individual component weights show no obvious minima as functions of the minimum bed pressure. When these weights are combined, however, the plot of total variable weight vs. minimum bed pressure exhibits a minimum total variable weight of 3.9 lb at slightly less than 1.0 atma. A desirable relative weight range between the minimum weight and 5% above the minimum weight was defined to yield a desirable total variable weight range of 3.9 to 4.1. This corresponds to a range of the minimum bed pressure of about 0.8 to 1.0 atma, which is a desirable PVSA operating range for this Example. In this desirable pressure range, the weight of the adsorbent is between a lower value of 1.0 lb and an upper value of 1.5 lb, the weight of the primary gas mover is 1.1 lb, and the weight of the battery is between a lower value of 1.4 lb and an upper value of 2.0 lb.

EXAMPLE 17

The PVSA system of FIG. 1 was simulated using the cycle described in Tables 1 and 2 for product flow rates of 1 to 3 lpm, product delivery pressures between 1.2 and 1.6 atma, and run times between 1 and 3 hours. The PVSA system of FIG. 1 also was simulated using the cycle described in Tables 3 and 4 for the same product flow rates, product delivery pressures, and run times. For these simulations, the rechargeable battery provides between 0.02 and 0.17 KWh of power during the operating run time between maximum and minimum working charge. The total working capacity of the adsorbent in each adsorber bed during the cycles is between $1.2 \times 10^{-4}$ and $6.7 \times 10^{-4}$ lbmoles of nitrogen. The feed air compressor (the first compressor) moves between $1.14 \times 10^{-4}$ and $4.01 \times 10^{-4}$ lbmoles of pressurized feed air during the feed steps and the waste gas compressor (the second compressor) moves between $3.47 \times 10^{-4}$ and $9.96 \times 10^{-4}$ lbmoles of waste gas during the depressurization and evacuation steps.

A summary of the results from Examples 1-16 is given in Table 5. These results were utilized to define desirable operating ranges for the weights of the adsorbent, primary gas mover, and battery as functions of the product flow rate. This was effected by plotting values of the upper and lower weights corresponding to the upper and lower values of the minimum bed pressure ranges for each of the variable-weight components defined in Examples 1-16 as functions of product flow rates. Linear boundaries to define a desirable operating region in terms of weight vs. product flow rate then were constructed for each component so that all upper and lower values of the minimum weights were included in this optimum operating region. In addition, ranges of the minimum weight of the battery were normalized to a unit run time and plotted as functions of the product flow rate to determine an optimum operating region in terms of this normalized variable. Based on these Examples, the minimum bed pressure typically falls between 0.25 and 1.0 atma, and may be in the range of 0.45 and 0.8 atma.

TABLE 5

Summary of Examples 1 through 16

| Example No. | Product Flow, lpm | Product Press., atma | Run Time, hr | No of Beds | Primary Gas Mover Type | Minimum Bed Pressure, atma | | Total Variable Weight, lb | |
|---|---|---|---|---|---|---|---|---|---|
| | | | | | | Minimum | Range | Minimum | Range |
| 1 | 3 | 1.6 | 1 | 5 | Scroll | 0.7 | 0.4-0.9 | 3.6 | 3.6-3.8 |
| 2 | 3 | 1.6 | 1 | 5 | Diaphragm | 0.7 | 0.5-0.9 | 2.8 | 2.8-3.0 |
| 3 | 2 | 1.4 | 2 | 5 | Scroll | 0.7 | 0.6-0.9 | 2.9 | 2.9-3.1 |
| 4 | 2 | 1.4 | 2 | 5 | Diaphragm | 0.8 | 0.6-0.9 | 2.3 | 2.3-2.5 |
| 5 | 1 | 1.2 | 3 | 5 | Scroll | 0.7 | 0.6-0.8 | 1.5 | 1.5-1.6 |
| 6 | 1 | 1.2 | 3 | 5 | Diaphragm | 0.7 | 0.6-0.8 | 1.2 | 1.2-1.3 |
| 7 | 3 | 1.6 | 3 | 5 | Scroll | 0.9 | 0.8-1.1 | 4.8 | 4.8-5.0 |
| 8 | 3 | 1.6 | 3 | 5 | Diaphragm | 0.9 | 0.8-1.0 | 4.0 | 4.0-4.2 |
| 9 | 3 | 1.6 | 1 | 4 | Scroll | 0.7 | 0.5-0.9 | 3.2 | 3.2-3.4 |
| 10 | 3 | 1.6 | 1 | 4 | Diaphragm | 0.7 | 0.5-0.9 | 2.7 | 2.7-2.9 |
| 11 | 2 | 1.2 | 2 | 4 | Scroll | 0.8 | 0.6-0.9 | 2.6 | 2.6-2.8 |
| 12 | 2 | 1.2 | 2 | 4 | Diaphragm | 0.8 | 0.6-0.9 | 2.3 | 2.3-2.4 |
| 13 | 1 | 1.2 | 3 | 4 | Scroll | 0.7 | 0.6-0.9 | 1.4 | 1.4-1.5 |
| 14 | 1 | 1.2 | 3 | 4 | Diaphragm | 0.7 | 0.6-0.8 | 1.2 | — |
| 15 | 3 | 1.6 | 3 | 4 | Scroll | ~1.0 | 0.8-1.1 | 4.4 | 4.4-4.6 |
| 16 | 3 | 1.6 | 3 | 4 | Diaphragm | ~1.0 | 0.8-1.0 | 3.9 | 3.9-4.1 |

Figure 18:
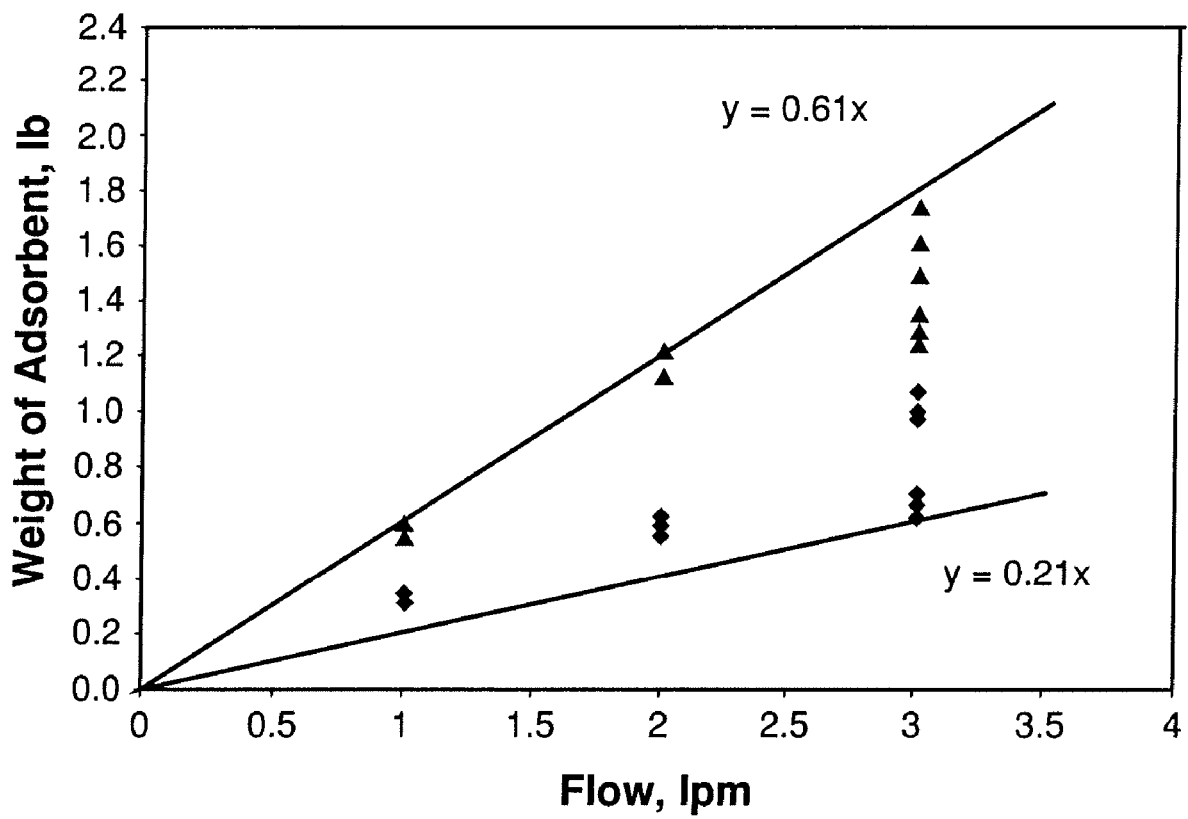
FIG. 18 is a plot of adsorbent weights vs. product flow rate for Examples 1-16.

The resulting plots and desirable operating regions for the individual variable-weight components are shown in FIGS. 18, 19, 20, and 21. FIG. 18 illustrates a desirable operating region bounded by (a) a lower line drawn through the origin and the lower weight of the adsorbent weight range for the product flow rate of 3 lpm and (b) an upper line drawn through the origin and the upper weight of the adsorbent weight range for the product flow rate of 1 lpm. All upper and lower weights of the adsorbent for product flow rates of 1, 2, and 3 lpm thus fall within the desirable operating region described by the upper and lower lines of FIG. 18.

Figure 19:
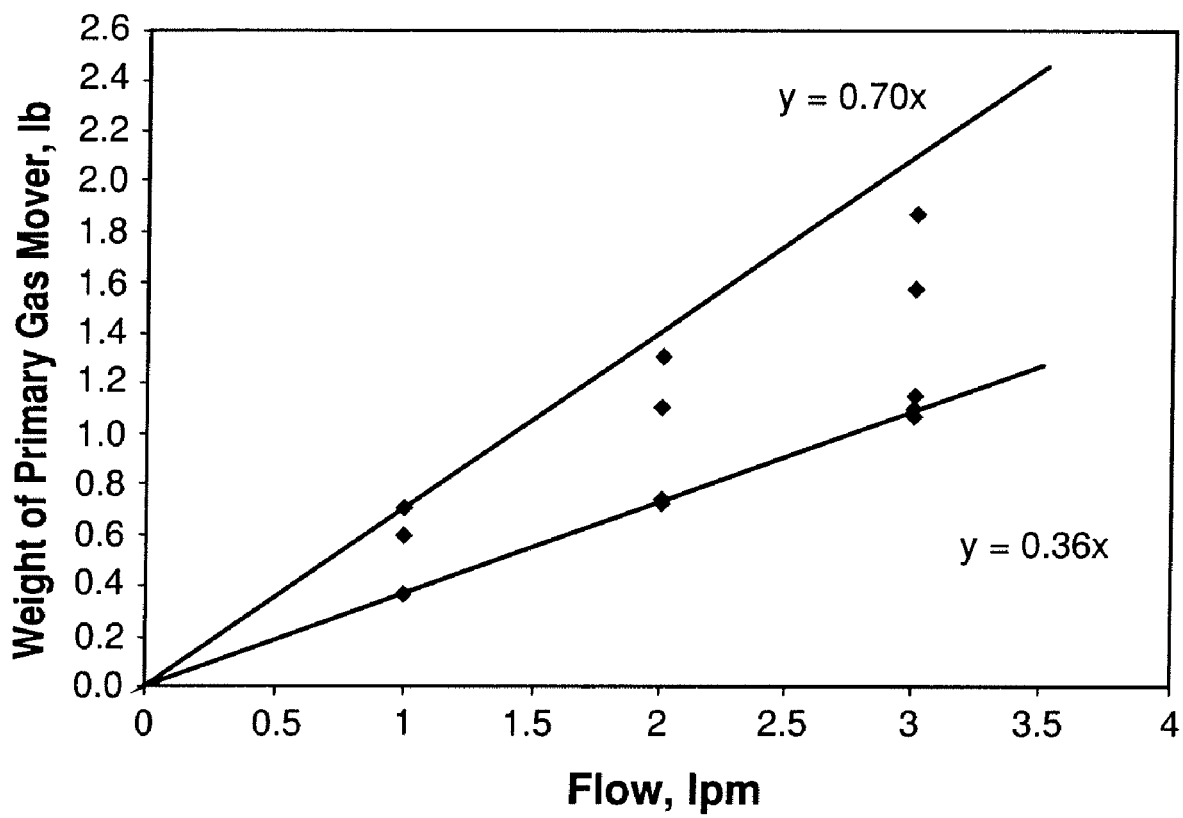
FIG. 19 is a plot of the weights of the primary gas mover vs. product flow rate for Examples 1-16.

FIG. 19 indicates that the desirable range of the weights of the primary gas movers lie between and include the weights of the scroll-type and diaphragm-type feed air and waste gas compressors which define the upper and lower lines, respectively.

Figure 20:
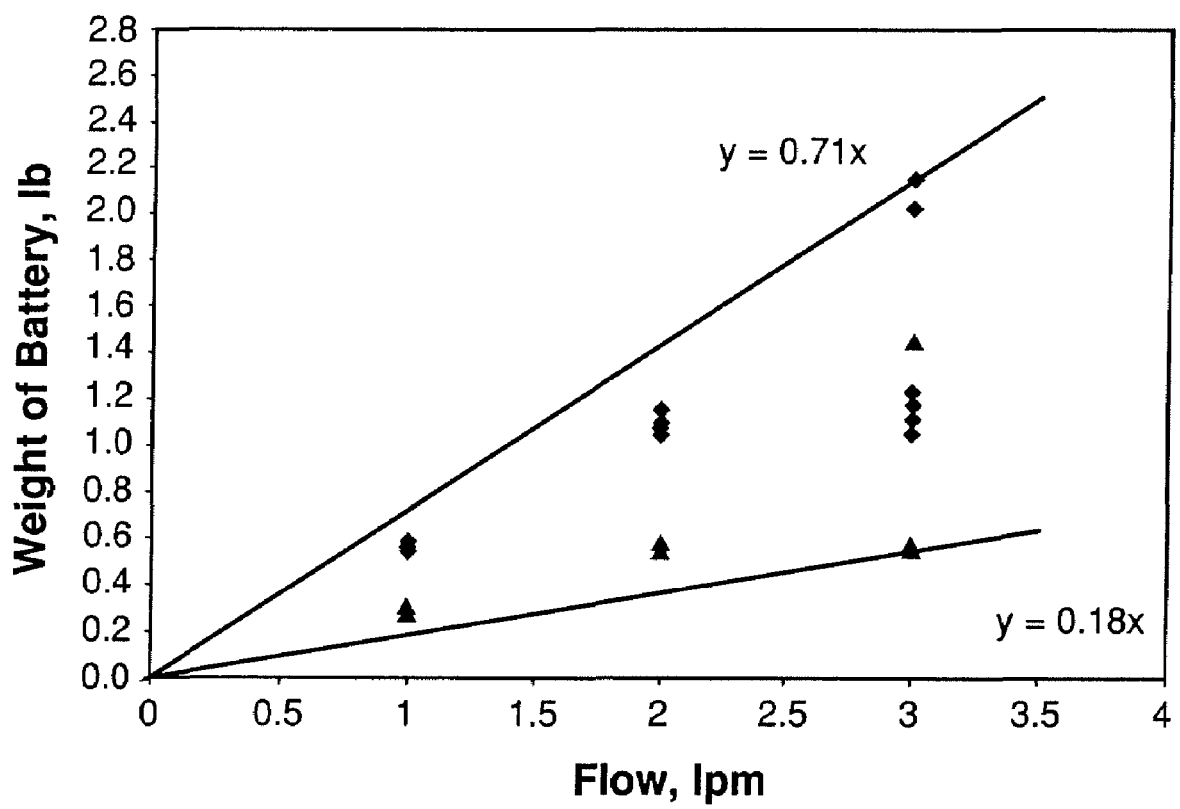
FIG. 20 is a plot of the battery weights vs. product flow rate for Examples 1-16.

FIG. 20 illustrates a desirable operating region bounded by upper and lower lines drawn through the origin and the upper and lower battery weights of the Examples at 3 lpm product flow rates. All upper and lower weights of the variable-weight battery for product flow rates of 1, 2, and 3 lpm thus fall within the desirable operating region described by the upper and lower lines.

Figure 21:
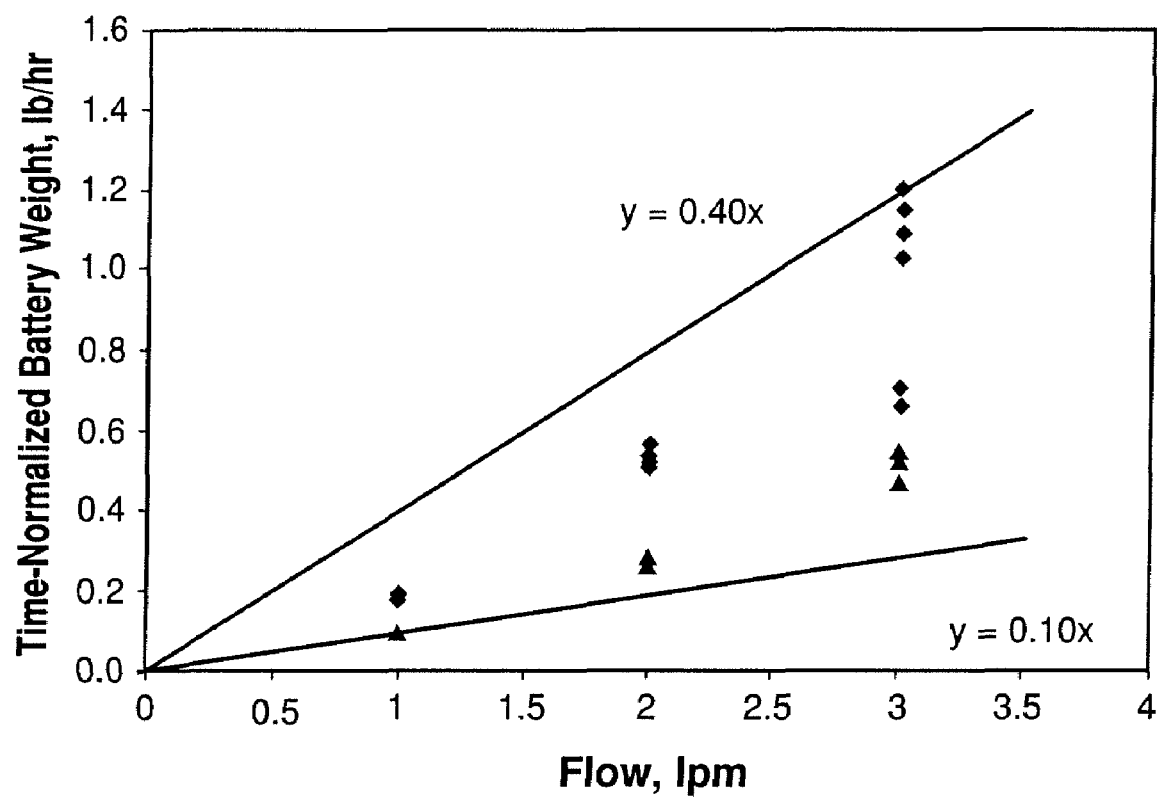
FIG. 21 is a plot of the time-normalized battery weights vs. product flow rate for Examples 1-16.

FIG. 21 illustrates a desirable operating region bounded by (a) a lower line drawn through the origin and the lower value of the time-normalized battery weight range corresponding to the Examples at 1 lpm product flow rate and (b) an upper line drawn through the origin and the upper value of the time-normalized battery weight range corresponding to the Examples at a product flow rate of 3 lpm. All upper and lower values of the time-normalized battery weight for product flow rates of 1, 2, and 3 lpm thus fall within the desirable operating region described by the upper and lower lines of FIG. 21.

The optimization methods described above thus cover the operation of four bed and five bed PVSA system for production rates of 1 to 3 lpm of 93 mole % oxygen in a product pressure range of 1.2 to 1.6 atma for periods of 1 to 3 hours of continuous run time. The corresponding optimum weight ranges for individual components were defined analytically for the desirable operating ranges of the minimum bed pressure. In addition, desirable operating regions were defined analytically in terms of weight vs. product flow rates for the individual variable-weight components. Also, desirable operating regions were defined analytically in terms of weight vs. product flow rates for the total weights of the combined variable-weight. These are summarized below.

The desirable operating regions described above and illustrated in FIGS. 18, 19, 20, and 21 may be expressed as follows for the individual variable-weight components:

(a) for the weight of the adsorbent, $W_a$, $$0.21 F_p < W_a < 0.61 F_p;$$

(b) for the weight of the primary gas mover, $W_p$, $$0.36 F_p < W_p < 0.70 F_p;$$

(c) for the weight of the battery, $W_b$, $$0.18 F_p < W_b < 0.71 F_p; \text{ and}$$

(d) for the battery weight on a time-normalized basis, $$0.10 F_p t_r < W_b < 0.40 F_p t_r.$$

In these expressions, $F_p$ is the product flow rate in liters per minute (at 23° C. and 1 atma), weight is in pounds, and time $t_r$ is in hours. The desired operating characteristics of the PVSA systems described above may be characterized by any of the above expressions.

By combining the expressions in (a), (b), and (c) above, the total variable weight, $W_t$, may be expressed as $$0.75 F_p < W_t < 2.02 F_p$$

where $W_t$ is in pounds. The combined weight of the variable-weight components of a PVSA system designed for generating 1 lpm of 93 mole % oxygen thus may lie between 0.75 and 2.02 pounds and a system designed for generating 3 lpm of 93 mole % oxygen thus may lie between 2.25 and 6.06 pounds. This expression may be extended to product flow rates above 3 lpm and below 1 lpm to determine the total variable weight of the PVSA system components. For example, the expression may be used to determine the total variable weight between 0.5 and 5 lpm, and this weight would range between 0.375 lb and 1.01 lb for a 0.5 lpm system and between 3.75 lb and 10.1 lb for a 5 lpm system.

The invention claimed is:

1. A method for producing an oxygen-rich product gas comprising
   (a) providing a primary gas mover including a first compressor for compressing atmospheric air to provide pressurized feed air and a second compressor adapted to compress an oxygen-depleted waste gas from subatmospheric pressure to atmospheric pressure, a drive motor for driving the first and second compressors, and a rechargeable battery for providing power to the drive motor, wherein the rechargeable power supply is characterized by an operating run time between maximum and minimum working charge;
   (b) providing a pressure/vacuum swing adsorption system adapted to separate the pressurized feed air into the oxygen-rich product gas and the oxygen-depleted waste gas, wherein the adsorption system comprises a plurality of adsorber beds containing adsorbent; and
   (c) operating each of the adsorber beds in turn through an adsorption cycle including at least the repeating steps of feed/provide product, depressurization, evacuation, and repressurization;
   wherein the method is characterized by any of the operating parameters
      (1) the rechargeable battery provides between 0.02 and 0.17 KWh of power during the operating run time between maximum and minimum working charge;
      (2) the total working capacity of the adsorbent in each adsorber bed during the adsorption cycle is between $1.2 \times 10^{-4}$ and $6.7 \times 10^{-4}$ lbmoles of nitrogen;
      (3) the first compressor moves between $1.14 \times 10^{-4}$ and $4.01 \times 10^{-4}$ lbmoles of pressurized feed air during the feed/provide product step; and
      (4) the second compressor moves between $3.47 \times 10^{-4}$ and $9.96 \times 10^{-4}$ lbmoles of waste gas during the depressurization and evacuation steps.

2. The method of claim 1 wherein the pressure/vacuum swing adsorption system has four adsorber beds and each of the adsorber beds undergoes in turn a series of adsorption cycle steps which comprise
   (A) a feed/make product step wherein the pressurized feed air is introduced into a feed end of the bed while the oxygen-enriched product gas is withdrawn from a product end of the bed;
   (B) a feed/make product/provide repressurization step wherein the pressurized feed air is introduced into a feed end of the bed while an oxygen-enriched product gas is withdrawn from a product end of the bed, and wherein a portion of the product gas is used for pressurizing another bed undergoing its final repressurization step;

(C) a depressurization step in which the bed is depressurized by withdrawing gas therefrom, wherein at least a portion of the gas withdrawn therefrom is transferred to another bed undergoing a repressurization step;

(D) a provide purge step in which the bed is further depressurized by withdrawing gas therefrom, wherein at least a portion of the gas withdrawn therefrom is transferred to another bed undergoing a purge step;

(E) an evacuation step in which gas is withdrawn from the feed end of the bed until the bed reaches a minimum subatmospheric bed pressure;

(F) a purge step in which the bed is purged by introducing purge gas into the product end of the bed while continuing to evacuate the bed, wherein the purge gas is provided from another bed undergoing step (D);

(G) a repressurization step in which pressurization gas is introduced into the product end of the bed, wherein the pressurization gas is provided from another bed undergoing step (C); and (H) a final repressurization step in which product gas from another bed is introduced into the product end of the bed.

3. The method of claim 1 wherein the minimum bed pressure is between 0.25 and 1.0 atma.

4. The method of claim 1 wherein the minimum bed pressure is between 0.45 and 0.8 atma.

5. The method of claim 1 wherein the pressure of the oxygen-enriched product gas is between 1.2 and 1.6 atma.

6. The method of claim 1 wherein the oxygen-enriched product gas is provided at a flow rate in the range of 0.5 to 3.0 liters per mm (defined at 23° C. and 1 atma pressure).

7. A method for producing an oxygen-rich product gas comprising
  (a) providing a primary gas mover including a first compressor for compressing atmospheric air to provide pressurized feed air and a second compressor adapted to compress an oxygen-depleted waste gas from subatmospheric pressure to atmospheric pressure, a drive motor for driving the first and second compressors, and a rechargeable battery for providing power to the drive motor, wherein the rechargeable power supply is characterized by an operating run time between maximum and minimum working charge;
  (b) providing a pressure/vacuum swing adsorption unit adapted to separate the pressurized feed air into the oxygen-rich product gas and the oxygen-depleted waste gas, wherein the adsorption unit comprises a plurality of adsorber beds containing adsorbent selective for the adsorption of nitrogen from air, and
  (c) operating each of the adsorber beds in turn through an adsorption cycle including at least the repeating steps of feed/provide product, depressurization, evacuation, and repressurization;

wherein the minimum pressure in the evacuation step is between 0.35 and 1.00 atma.

* * * * *